US005843762A

United States Patent [19]
Moll

[11] Patent Number: 5,843,762
[45] Date of Patent: Dec. 1, 1998

[54] METHOD FOR THE HIGH YIELD, AGRICULTURAL PRODUCTION OF ENTEROMORPHA CLATHRATA

[75] Inventor: Benjamin Moll, Port Matilda, Pa.

[73] Assignee: Desert Energy Research, Inc., Port Matilda, Pa.

[21] Appl. No.: 676,468

[22] Filed: Jul. 8, 1996

Related U.S. Application Data

[63] Continuation of Ser. No. 398,947, Mar. 2, 1995, abandoned.
[51] Int. Cl.⁶ .............................. A23K 1/18; A01N 63/00; C12N 1/12; C12P 1/00
[52] U.S. Cl. ........................ 435/257.1; 424/93.1; 426/61; 426/807; 435/41; 435/946
[58] Field of Search .................................. 435/41, 257.1, 435/946; 426/61, 807; 424/93.1

[56] References Cited

U.S. PATENT DOCUMENTS

| P.P. 4,511 | 3/1980 | Avron et al. | Plt./100 |
|---|---|---|---|
| P.P. 6,169 | 5/1988 | Nonomura | Plt./100 |
| 4,253,271 | 3/1981 | Raymond | 47/1.4 |
| 4,320,594 | 3/1982 | Raymond | 47/1.4 |
| 4,333,263 | 6/1982 | Adey | 47/1.4 |
| 4,869,017 | 9/1989 | Bird et al. | 47/1.4 |
| 4,958,460 | 9/1990 | Nielson et al. | 47/1.4 |
| 4,996,389 | 2/1991 | Bird | 800/200 |
| 5,270,175 | 12/1993 | Moll | 435/41 |

OTHER PUBLICATIONS

Harlin, et al., Marine Biology, 1981, pp. 221–230, Abst.
Schupp, et al., Ecology (Tempe) 75 (4) 1994, pp. 1172–1185, Abst.
Turner, et al., Aquaculture 53(2), 1986, pp. 145–156, Abst.
Shellem, et al., Bot. MAR 25 (11), 1982 pp. 541–550, Abst.
Fitzgerald, et al., Bot. MAR 21 (4) 1978 pp. 207–220, Abst.
Cote, W.A., Ed. (1983). Biomass Utilization. Plenum Press, New York. Nato ASI Series A, vol. 67.
Technical Insights, Inc. Biomass Process Handbook. Fort Lee, New Jersey.
Spencer, D.F. (1991). A Preliminary Assessment of Carbon Dioxide Mitigation Options. Annual Review of Energy and Environment. 16:259–273.
Gao, K., K.R. McKinley (1994). Use of Macroalgae for Marine Biomass Production and CO2 Remediation: A Review. Journal of Applied Phycology 6:45–60.
Ventura, M.R. (1994) Nutritional Value of Seaweed (Ulva Rigida) for Poultry. Animal Feed Science and Technology, 49:87–94.
Stephenson, W.A. (1973). Seaweed in Agriculture and Horticulture. EP Publishing, Yorkshire, U.K.
Lobban, C.S., P.J. Harrison (1994) Seaweed Ecology and Physiology. Cambridge University Press. Cambridge.
Quarmby, D., S.F. Allen (1989) pp. 172–175 in "Chemical Analysis of Ecological Materials", Allen,S.E., Ed. Blackwell Scientific, Boston.

Fontes, A.G., J. Moreno, M.A. Vargas (1988) Analysis of the Biomass Quality and Photosynthetic Efficiency of a Nitrogen–Fixing Cyanobacterium Grown Outdoors With Two Agitations Systems. Biotechnology and Bioengineering, 34:819–824.
Ryther, J.H. (1985). Technology for the Commercial Production of Biomass, in "Energy Applications of Biomass", M.Z. Lowenstein, Ed. Elsevier, New York, pp. 177–188.
Schramm, W. (1991) Cultivation of Attached Seaweed. In "Seaweed Resources in Europe: Uses and Potential", pp. 379–408. M.D. Guiry and G. Bluunden, Eds. John Wiley & Sons Ltd, London.
La Pointe, J.L. Ryther (1978). Some Aspects of the Growth and Yield of *Gracilaria Tikvihae* in Culture. Aquaculture, 15: 185–193.
Laws, E.A., J.L. Berning (1991). Photosynthetic Efficiency Optimization Studies With the Macroalga *Gracilaria Tikiva*: Implications for CO2 Emission Control Form Power Plants. Bioresource Technology 37:25–33.
Benneman, J.R, J.C. Weissmann, R.P. Goebel, D.C. Augenstein (1985). Microalgae Fuel Economics. In "Algal Biomass Technologies", Barclay, W.R. and MacIntosh, R.P. McIntosh, Eds. J.Cramer, Berlin.
Blakeslee, M. (1986). Determination of Carbon Concentration Effects on Photosynthesis: A pH Independent Approach. In "Algal Biomass Technologies", W.R. Barclay, R.P. McIntosh, Eds. J. Cramer, Berlin.
Huguenin, J.E., J. Colt (1989). Design and Operating Guide for Aquaculture Seawater Systems. Elsevier, New York.
Fong, P., T.C. Foin, J.B. Zedler (1994) A Simulation Model of Lagoon Algae Based On Nitrogen Competition and Internal Storage. Ecological Monographs 64:225–247.

(List continued on next page.)

Primary Examiner—David M. Naff
Assistant Examiner—Deborah K. Ware
Attorney, Agent, or Firm—Oppenheimer Wolff & Donnelly LLP

[57] ABSTRACT

A method is provided for the high yield, agricultural production of *Enteromorpha clathrata* involving repeated steps of supplying brackish or seawater to a pond containing *Enteromorpha clathrata*. The method involves the steps of (a) supplying a first volume of water, the water selected from the group consisting of brackish and seawater supplemented with at least one fertilizer, wherein the water is conducive to growing *Enteromorpha clathrata*, to a first predetermined depth in a pond; (b) introducing *Enteromorpha clathrata* into the conducive water; (c) growing the *Enteromorpha clathrata* for a predetermined time, wherein the conducive water becomes less conducive to growing *Enteromorpha clathrata*; (d) withdrawing at least partially the less conducive water after the time, (e) refilling the pond with a second volume of water, the second volume of water selected from the group consisting of brackish and seawater supplemented with at least one fertilizer, wherein said water is conducive to growing *Enteromorpha clathrata*, to a second predetermined depth; and (f) repeating steps c, d and e wherein the *Enteromorpha clathrata* grows into a layer of filaments, a portion of the filaments extending above the surface of the water and being exposed to the air. In addition, a method for producing feed for mammals and poultry is also disclosed.

61 Claims, 7 Drawing Sheets

OTHER PUBLICATIONS

Wilde, Beneman (1993) Bioremoval of Heavy Metals by the Use of Microalgae. Biotech Adv. 11: 781–812.

Haratonidis Jager Schwantes (1983) Accumulation of Cadmium, Zinc, Copper and Lead by Marine Macrophycae Under Culture Conditions. Angewandte Botanik 57: 311–330.

Moll, Benjamin & Deikman, Jill (1995) *Enteromorpha Clathrata*: A Potential Seawater–Irrigated Crop, Bioresource Technology 52: 225–260.

METHOD FOR THE HIGH YIELD, AGRICULTURAL PRODUCTION OF ENTEROMORPHA CLATHRATA

RELATED APPLICATIONS

This is a continuation of co-pending application, Ser. No. 08/398,947, filed on Mar. 2, 1995 now abandoned.

FIELD OF THE INVENTION

The present invention relates generally to the culture of algae. More specifically, it relates to a method of growing *Enteromorpha clathrata* algae for high yield, agricultural purposes. The present invention further relates to a diploid, stress-tolerant strain of *Enteromorpha clathrata* cv. Berkeley and to certain haploid derivatives of *Enteromorpha clathrata* cv. Berkeley grown according to the disclosed method.

DESCRIPTION OF RELATED ART

The publications and other reference materials referred to herein to describe the background of the invention and to provide additional details regarding its practice are hereby incorporated by reference. For convenience, the reference materials are numerically referenced and identified in the appended bibliography.

A wide variety of plant materials are currently being employed for the production of biomass feeds, starch and ethanol. Biomass, for example, is plant material without any specially valuable composition. Biomass is used for direct burning as fuel, or as a feedstock for production of valuable substances such as ethanol. Biomass can be produced by several methods [1,2]. Most crops produce residue, i.e., what is left after the valuable part of the crop, such as grain, has been taken. Because the cost of production is born by the harvested portion of the crop, the crop residue could be thought of as being free. Even so, there are costs associated with its use. The economical use of biomass requires very low cost transformation into some more useful form, e.g., by saccharification and fermentation to ethanol. This process must operate on a very large scale to be economically feasible. The large amount of crop residue required for a large scale operation means that the residue must be trucked long distances with resultant shipping costs. Furthermore, the removal of residues from crop lands can result in increased erosion and decreased water penetration, resulting in large long term costs for residue removal. The potential yield of biomass from crop residues is far smaller than expected needs for production of renewable fuels, so additional sources are required.

Special crops can be grown for the purpose of producing biomass, for example woody plants such as fast-growing cottonwood, or non-woody plants such as high-yield grasses. Such energy crops are grown in regions that are generally suitable for the cultivation of food crops, so that while they do have the potential to make a substantial contribution to future energy supplies, it would be necessary to use cropland and as a result reduce our capacity to produce food.

New sources of biomass are needed that can be produced at low cost in regions unsuited to the production of traditional food crops.

Feed is grain or other plant or animal substance that is fed to animals. Many different crops are used as feed. A large proportion of the feed produced in the United States is maize. Other crops are also used, including other grain crops and legumes, especially soybeans. Different crops have different values as feed. Crops with high cellulose content are of value mainly in feeding ruminants and other animals which can digest cellulose. Crops with high starch content can be used more widely. Feed must provide for other nutritional needs besides energy needs provided for by cellulose or starch. For example, protein must be available in feed. Feed may be a mixture of substances from different sources, designed to provide an adequate diet at low cost. The constituents of feed may be given as harvested, or they may be processed. For example, feed may be ground or crushed, feed components may be cooked or treated chemically, different components may be mixed, and feed may be pelleted [3].

Animal feeds are essential to a productive agricultural industry that provides consumers with animal products. There are large regions of the world in which feed is in short supply. New crops are needed that can be grown with good yields at low cost in areas that are now unproductive.

Starch is a well characterized polymer of glucose that is the principal storage form of carbohydrate in higher plants and some algae, including green algae. Starch can be purified from a variety of plant sources with a composition high in starch, including grains and potatoes. In the United States, most starch is derived from maize. Starch is obtained from grains by milling the grain to small particles, a fraction of which are starch grains. The starch fraction is separated from the non-starch fraction by floatation or centrifugation and washed [4]. Starch can be used for several purposes, including for production of high-fructose syrup, for production of glucose syrup, as a food ingredient, for production of adhesives and for production of ethanol [5]. Crops that can be used for starch production will be profitable if the derived starch can be sold at competitive prices. New crops are needed that can be grown with good yields at low cost in areas that are now unproductive.

Ethanol is a common type of alcohol that can be used for many purposes, including use as a fuel or a fuel additive. It can be produced by fermentation of sugar. Sugar may be derived from starch or cellulose or other sugar polymer. In the US about 1 billion gallons per year of ethanol are produced from corn starch for fuel use [4]. The total United States market for high quality liquid fuel is over 100 billion gallons per year. Projects now in progress will make raw materials other than corn starch economical for ethanol manufacture, but even so only a small fraction of the potential market for fuel ethanol can be filled by these technologies if we retain most of our food production capacity. There is a tremendous unfilled need for a clean burning renewable fuel such as ethanol.

For all of the above industries, there are satisfactory technical methods of production. The problem lies not in the ability to produce these commodities, but in the ability to produce them in much larger quantities than now produced, at low cost, preferably in regions where agricultural productivity is now low.

Algae can be used to satisfy the needs described above. For example, algae can be used as biomass [6, 7]. For example, algae can be used as a feedstock for the production of methane, or alcohol or other chemicals. Algae can be used as feed for animals. For example, algae and can be used as a feed ingredient to feed chickens [8] and cattle [9]. For this purpose, algae that are particularly high in starch and protein, as opposed to the less digestible cell wall material, are particularly desirable. Algae can be used as food for humans. Approximately 1.7 million tons are produced annually for this purpose [10].

Algae that store starch as a storage product could be used as a source of starch. Starch can be purified from algae using well known methods, for example, [11], or by using methods used for purification of starch from grains, for example, milling followed by centrifugation. Starch derived from algae can, of course, be used for all the purposes that starch in general is used for, including the production of syrups, adhesives and ethanol.

Several algae culture methods exist or have been proposed. There are commercial and experimental systems for microalgae and for macroalgae.

Microalgae are grown commercially as health food supplements and as a source of beta-carotene. Production costs are over $10,000 per dry ton. Intensive production methods use concrete lined raceways with rapid water circulation. Experimental systems include inventions designed to improve harvesting economics [12] and inventions designed to improve yields [13, 14, 15]. High yields require aeration and vigorous mixing or carbon dioxide supplementation.

Macroalgae are grown commercially, mainly in the orient for human food. Methods are non-intensive. Costs are moderate to high, $500 to $1,000 per ton dry weight, depending on the species and yields are moderate, comparable to other forms of agriculture [16]. Only certain sites are suitable for some culture methods, so applications are restricted. These techniques, while commercially viable, are limited in yield, and because of costs are not competitive for biomass or animal feed uses. Cultivated species include Gracilaria, Porphyra, Laminaria, Eucheuma, Monostroma, Ulva, and Enteromorpha [16]. Low cost culture has been investigated outside of the orient [17], but not commercialized. Experimental high yield systems have also been proposed [10, 17 (review), 18, 19] and commercial application has been attempted [10]. These systems all utilize either very large water flows or $CO_2$ supplementation to provide inorganic carbon for photosynthesis. As a consequence, both capital expenditures and operating costs are too high for commercial operation. For example, the culture of Gracilaria has been studied as a possible energy crop. Very high yields can be obtained, corresponding to as much as 150 tons dry weight/hectare-year [19]. To obtain these yields, 15 exchanges of medium per day were used in 30 cm deep ponds, i.e., 4,500 liters/$m^2$-day. These water flows are too high for a low cost operation. In some cases $CO_2$ supplementation may be less costly, but is not expected to be commercially viable unless the crop has high value for some reason, or unless there is a credit for preventing CO2 from entering the atmosphere, e.g., from a power plant [20].

There are several alternatives to the algae for use as aquatic crops, including azolla, duckweed and water hyacinth, but all of these require fresh water, and are not competitive with marine algae.

Existing methods for growing algae at high yield have one major failure: the production cost is too high. The major elements of cost depend on the method under consideration, but important points include harvest expenses, especially for microalgae, pond construction expenses, and expenses associated with $CO_2$ supply such as water pumping, $CO_2$ supplementation and water stirring or circulation [21].

Harvest expenses can be very high, particularly in the case of microalgae which do not grow to high densities. A large volume of medium must be processed by some method, e.g., by centrifugation, to harvest the crop. Because of the expense of the required equipment, capital costs are high as a consequence. While other harvesting methods have been suggested, harvesting is an important issue in microalgal economics. Harvest expenses are typically much lower for macroalgae, and are compatible with low cost culture.

Pond construction expenses are a major factor in the economics of algal culture. Pond lining, e.g., with concrete or plastic, is very expensive. Lined ponds are required if high water flow rates or agitation are used. Even unlined ponds can be a substantial investment, depending on how much earth moving is required in their construction.

An important issue in high yield algal culture is the availability of $CO_2$ [22]. In particular, the $CO_2$ content of seawater is about 2 mM total inorganic carbon. Thus a 10 cm deep pond would contain about 0.2 moles of inorganic carbon per meter squared. Since a rapidly growing culture will fix over 1 mole of carbon in a day, it is clearly necessary to either supplement the carbon dioxide content of the water, or use considerably more water, at least 1000 liters/meter squared—day, or absorb carbon dioxide from the atmosphere. If $CO_2$ is supplemented, then added costs include spargers and a water circulation system, with resultant costs for suitable pond lining and energy for water circulation. If large amounts of water are pumped, then added costs include pumps and water distribution system, energy for water pumping, and pond size or lining suitable for the increased water flow. There are other stresses associated with low water exchange rates such as changes in pH, salinity and dissolved oxygen that make high water exchange rates seem necessary, although these do not appear to be such insurmountable obstacles as the lack of carbon dioxide. The resultant production costs are well established, and are sufficient to render high yield culture uneconomical [17]. There is, thus, a continuing need to develop systems for growing algae at a nonprohibitive cost.

SUMMARY OF THE INVENTION

In accordance with the present invention a method of growing *Enteromorpha clathrata* is presented. The method involves the steps of (a) supplying water, the water selected from the group consisting of brackish and seawater supplemented with at least one fertilizer, wherein the water is conducive to growing *Enteromorpha clathrata*, to a first predetermined depth in a pond; (b) introducing *Enteromorpha clathrata* into the conducive water; (c) growing the *Enteromorpha clathrata* for a predetermined time wherein the conducive water becomes less conducive after the predetermined time; (d) withdrawing at least partially the less conducive water after the predetermined time; (e) refilling the pond with a second volume of water, consisting of at least one of brackish and seawater supplemented with at least one fertilizer, wherein the second volume of water is conducive to growing the *Enteromorpha clathrata*, to a second predetermined depth, and (f) repeating steps c, d and e such that the *Enteromorpha clathrata* grows into a layer of filaments, a portion of the filaments extending above the surface of the water and being exposed to the air. Another feature of the instantly disclosed invention is *Enteromorpha clathrata* grown according to the method.

The high yield, agricultural production aspect of the present invention is based on the discovery in accordance with the present invention that stress-tolerant *Enteromorpha clathrata* cv. Berkeley may be grown at high yield in ponds without the introduction of exogenous $CO_2$. Such high yield growth without the introduction of exogenous $CO_2$ is obtained because the filaments of the Enteromorpha grow in such a manner that they extend above the surface of the water and are exposed to the air. It has been discovered that these filaments that are exposed to the air are able to absorb the $CO_2$ required for photosynthesis from the air. The method of the present invention is able to economically exploit this discovery to make feasible the high yield, agricultural production of *Enteromorpha clathrata* with low volumes of seawater usage.

Laboratory growth measurements indicated that *Enteromorpha clathrata* is capable of producing biomass at a rate of approximately 28 grams dry weight per square meter per day. If this rate could be maintained 365 days a year, it would result in a yield of over 100 metric tons per hectare per year. (After initial planting, Enteromorpha grows vegetatively indefinitely. If harvesting leaves enough plant material in the field to maintain productivity, neither harvesting nor crop establishment need to interrupt productivity.) High yields from *Enteromorpha clathrata* can be achieved without costly $CO_2$ supplementation or large water-flows. The combination of high yield and low production cost makes Enteromorpha ideal for seawater-irrigated desert agriculture. In this respect, it is different from previously studied algae. This result is of great significance to the search for additional sources of biomass, and to the search for ways to make desert regions agriculturally productive.

For use as an agricultural crop with minimum production costs, it is desirable to minimize water use and minimize chemical pH correction while maintaining high yields. The high productivity of Enteromorpha observed in high pH and high salinity conditions indicates that a management strategy with normal pH and salinity only part of the time will give high yields. It may be possible to grow Enteromorpha in shallow ponds that reach 2× salt concentration in several days. When medium is exchanged, rapid growth would occur, followed by a period of slower growth and starch accumulation as pH and salinity rise. In fact it has been discovered that there is no reduction in productivity with a one day exposure to 2.5× seawater. Growth is reduced in high salinity, so periodic exposure to water with low salinity is required for prolonged productivity.

Marine algae can make a large contribution to biomass production if they can be grown with seawater irrigation several kilometers from a water source, so that the potential culture area is large. Irrigation costs become excessive too far from a water-source, or if water requirements are too large. The salt tolerance observed in the Enteromorpha is sufficient to permit evaporation of 50% or more of the delivered volume of seawater.

Also presented in accordance with the present invention is a method of producing feed involving growing *Enteromorpha clathrata* according to the above method and further involving the steps of (a) harvesting the *Enteromorpha clathrata*; and (b) processing said harvested *Enteromorpha clathrata* to produce feed.

Still another aspect of the present invention is feed produced according to the instantly disclosed method.

Also presented in accordance with the present invention is a stress-tolerant selected diploid, *Enteromorpha clathrata* cv. "Berkeley," and several selected haploid derivatives thereof.

The above described and many other features and attendant advantages of the present invention will become better understood by reference to the following detailed description.

DETAILED DESCRIPTION OF THE PREFERRED EMBODIMENTS

I. GENERAL DESCRIPTION

Figure 1:
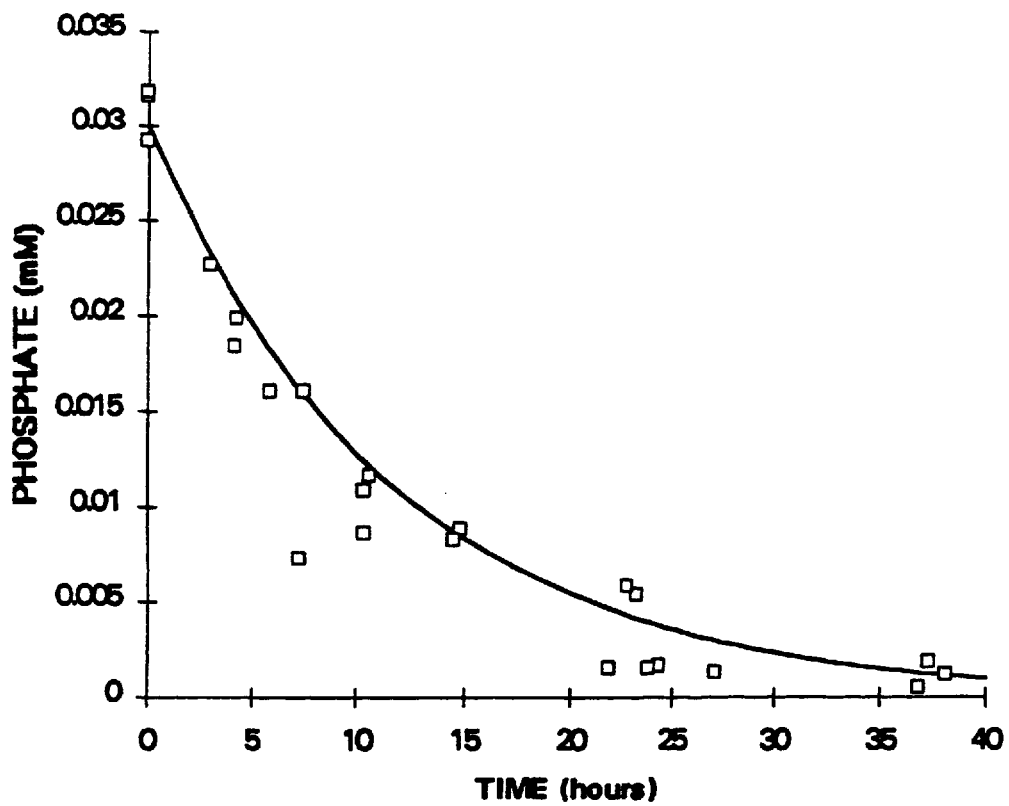
FIG. 1 is a graph showing the phosphate depletion time course. Data points are from four independent experiments, using 0.5 g fresh weight of tissue in 300 ml of medium. The solid line shows the expected time course of phosphate depletion assuming a rate constant of 0.050 liter $gfw^{-1}$ $hour^{-1}$.

In accordance with the present invention a method of growing *Enteromorpha clathrata* is presented. The method involves the steps of (a) supplying a first volume of water, the water selected from the group consisting of brackish and seawater supplemented with at least one fertilizer, wherein the water is conducive to growing *Enteromorpha clathrata*, to a first predetermined depth in a pond; (b) introducing *Enteromorpha clathrata* into the conducive water; (c) growing the *Enteromorpha clathrata* for a predetermined time, wherein the conducive water becomes less conducive to growing *Enteromorpha clathrata*; (d) withdrawing at least partially the less conducive water after the time, (e) refilling the pond with a second volume of water, the second volume of water selected from the group consisting of brackish and seawater supplemented with at least one fertilizer, wherein said water is conducive to growing *Enteromorpha clathrata*, to a second predetermined depth; and (f) repeating steps c, d and e wherein the *Enteromorpha clathrata* grows into a layer of filaments, a portion of the filaments extending above the surface of the water and being exposed to the air.

In accordance with the present invention, a floating mat of *Enteromorpha clathrata* is a floating culture in which the algal mass is not resting on the bottom of the pond, nor is it neutrally buoyant, but rather it is preferentially distributed toward the top of the water, with some parts of the plant body extending above the undisturbed surface of the water and being exposed to the air; at times, the water level may be too shallow for flotation to occur, even though the culture would still be described as floating in accordance with the present invention.

Prior to the present invention, the principal barriers to high yield in the culture of algae was the availability of $CO_2$. $CO_2$ has a very low solubility in water. This problem has been overcome in experimental cultures by either pumping large quantities of water past the crop, or by supplementing the growth medium with $CO_2$. Either strategy results in prohibitively high costs. The present invention uses air exposure of the filaments of the floating algal mat. It is generally known that the reason algal mats float is because of high oxygen concentration, which should inhibit photosynthesis. The present invention refutes this view, however, and shows instead that floating mats are highly productive in that they utilize $CO_2$ from the air. The ability for the algae to utilize $CO_2$ from the air for photosynthesis therefore eliminates the principal barrier to high yield, low cost algal culture.

Supplying water to the pond in accordance with the present invention is preferably performed by the use of pipe or channels using materials suitable for use with seawater such as earth, concrete or plastic, and using appropriate engineering practices [23]. The supplied water, in accordance with the present invention, consists of at least one of brackish and seawater. Brackish water in accordance with the present invention is water having a salinity between that of fresh water and that of water withdrawn from sea or ocean. Salinity in accordance with the present invention refers to the total salt content of water, mainly but not entirely due to sodium chloride. Other salts include, for example, potassium chloride, magnesium sulfate, calcium chloride and sodium bicarbonate. Salinity is measured, in accordance with the present invention, in terms of parts per thousand (ppt). Preferably, brackish water has a salinity of at least 10 ppt. Seawater in accordance with the present invention is water taken from a sea or ocean. The water preferably has a composition similar to that of seawater with respect to major ions, i.e. with approximately the following concentration of ions: sodium, 460 mM; chloride, 540 mM; potassium, 10 mM; magnesium, 53 mM; sulfate, 28 mM; calcium, 10 mM and with an initial pH of approximately 8.

II. SUITABLE STRAINS

The *Enteromorpha clathrata* introduced into the conducive water is preferably *Enteromorpha clathrata* cv. "Berkeley" or a haploid derivative thereof. Most preferably the introduced *Enteromorpha clathrata* is a haploid derivative of *Enteromorpha clathrata* cv. "Berkeley" selected from the group consisting of ZS1, ZS2, ZS3, ZS4, ZS5, ZS6, ZS7, ZS8, ZS9, ZS10, ZS11, ZS12, ZS13, ZS14, and ZS15.

This line of *Enteromorpha clathrata* is chosen for its high rates of dry weight accumulation, its high stress tolerance and its ability to absorb $CO_2$ from the air. *Enteromorpha clathrata* cv. Berkeley grows rapidly in a dense culture, forming a thick mat on the surface of the water. This thick mat is formed of numerous branches, or filaments, which extend above the surface of the water and are exposed to the air. Because the filaments extend above the surface of the water and are exposed to the air, *Enteromorpha clathrata* is able to absorb the $CO_2$ required for photosynthesis from the air. Thus, high-yield production growth of *Enteromorpha clathrata* can be carried out in shallow ponds without the introduction of exogenous $CO_2$. Both the high rate of dry-weight accumulation of *Enteromorpha clathrata* and the thick mat are related to its stress tolerance, since a thick mat will have high pH throughout and elevated salinity at the upper surface, where evaporation occurs. The well-being of the upper surface is essential to high productivity of *Enteromorpha clathrata*, because the upper layer has the best access to the light and $CO_2$ required for photosynthesis.

Also presented in accordance with the present invention is *Enteromorpha clathrata* comprising a haploid derivative of *Enteromorpha clathrata* cv. "Berkeley." Preferably, the haploid derivative of *Enteromorpha clathrata* cv. "Berkeley" is selected from the group consisting of ZS1, ZS2, ZS3, ZS4, ZS5, ZS6, ZS7, ZS8, ZS9, ZS10, ZS11, ZS12, ZS13, ZS14 and ZS15.

*Enteromorpha clathrata* cv. Berkeley is a cultivar which was isolated by screening for rapid growth in still water conditions. Essentially, this was done by using the methods of culture described below, and subculturing an alga that exhibited extremely rapid growth under the conditions given.

Small ponds were constructed by cutting down plastic pails 35 cm in diameter to 14 cm high. They were filled to a depth of 10 cm, and kept outside on a 1 m high platform in Emeryville, Calif. Ambient temperature varied from 15° to 20° C., with direct sunlight duration of up to 10 hours per day, depending on weather conditions. Initial isolations of algae from nature were carried out with water obtained from San Francisco Bay near Emeryville. Water was supplemented with 1 mM NaNO3 and 0.1 mM $NaH_2PO_4$ and 10 micrograms/liter vitamin B12 with weekly water exchange.

Collections of algae and rocks from shallow areas with little or no wave action were used to seed 16 small ponds of supplemented sea water. Deionized water was added to maintain water volume at 75 to 100% of initial volume. None of the algae deliberately collected, including Ulva and Enteromorpha species, showed prolonged growth in these conditions. In one pond, several rapidly growing algae were observed after 4 weeks.

A secondary screen for tolerance to high salt resulted in the survival of one individual. This was subsequently identified as *Enteromorpha clathrata*. It is tubular, the hollow filaments having walls one cell thick. Branching is prolific. Most species of Enteromorpha either do not exhibit branching or branch to limited degree, e.g., the main axis may form branches, but branches rarely arise on the secondary branches. In *Enteromorpha clathrata*, branches can arise from secondary, tertiary or higher order branches without limit. While other species of Enteromorpha have been described with this unlimited branching pattern, these are probably *E. clathrata* adapted to different habitats. In nutrient supplemented conditions *E. clathrata* grows profusely and forms a tangled mat that floats on the surface of the water. When mature, some filaments become gas filled.

*E. clathrata* was obtained in pure culture by growing in sterile supplemented seawater, with kanamycin (1000 mg/l) and streptomycin (1000 mg/l), antibiotics to which it is insensitive. Transfer to media without antibiotics but supplemented with glucose showed no contamination. In addition, Enteromorpha are fresh water tolerant and are selected for their tolerance to heat.

The Berkeley cultivar is diploid. It has been used to generate a series of haploid derivatives, ZS1, ZS2, ZS3, ZS4, ZS5, ZS6, ZS7, ZS8, ZS9, ZS10, ZS11, ZS12, ZS13, ZS14, and ZS15. Haploids are useful for three reasons. First, unlike diploids, they are genetically stable in the field. Their genetic complement can only change if gametes from outside the culture area mate with gametes from the crop plants. Diploids will give rise to haploid derivatives which are genetically and phenotypically different from the parental type, without any outside influence. Second, haploids express genetic traits that are recessive. Genetic selection for agronomic trains can be done on the haploid generation, in marked contrast to the situation in high plants. Third, breeding programs in higher plants often utilize highly inbred lines that are homozygous for almost all genes. The haploid lines of *Enteromorpha clathrata* serve the purposes of the highly inbred lines of higher plants breeding, i.e., they serve as breeding stock that will give progeny with predictable characteristics.

Certain haploid lines exhibit traits that are useful for field performance, at least in certain circumstances. For example, some haploid lines show tolerance of prolonged exposure to fresh water. This is valuable in areas where there is a possibility of prolonged rainfall, exposing the crop to fresh water for more than a few hours. As a further example, certain haploid lines exhibit tolerance to elevated temperatures, surviving exposure to up to 42° C. This trait is useful for production sites in desert areas with maximum air temperatures of about 42° C.

The methods described herein are suitable for the high-yield culture of *Enteromorpha clathrata* cv. Berkeley. Other strains may be isolated as described above, and their nutrient uptake, growth rate and response to stress characterized. Strains similar in these respects to *Enteromorpha clathrata* cv. Berkeley can also be grown with the methods described herein. Uncharacterized strains cannot necessarily be cultured using these methods, which are intended not as a general method of culture, but rather as a low-cost, high-yield method of culture applicable only to certain stress-tolerant, highly productive genotypes.

III. IRRIGATION AND POND DESIGN

In accordance with the present invention the algae *Enteromorpha clathrata* is introduced into the conducive water. Preferably, the Enteromorpha is initially introduced into the pond from a stock culture in the form of filaments about 2 cm long or longer in an amount sufficient to give essentially complete coverage of the pond surface, about 500 grams fresh weight per $m^2$. The introduced *Enteromorpha clathrata* is then grown for a predetermined time. Preferably the time is between 12 and 48 hours.

After the *Enteromorpha clathrata* is grown for the predetermined time, the water in the pond becomes less conducive to the growth of *Enteromorpha clathrata*. This condition is exhibited by reduced growth rate of Enteromorpha. In favorable conditions, the growth rate is preferably above 20 grams dry weight per $m^2$-day in conducive medium. Certain conditions are expected to result in reduced growth, such as exhaustion of nutrients such as nitrogen, phosphorus, iron or other nutrients, prolonged salinity over 70 ppt, or prolonged pH above 10.1.

After growing the *Enteromorpha clathrata* for a predetermined time, the less conducive water is at least partially withdrawn and the pond is then refilled with conducive water to a second predetermined depth, which is preferably the same as the first predetermined depth.

Partially withdrawing the less conducive water followed by partial refilling provides the advantage of better mixing than operation with continuous water flow. Withdrawal of substantially all of the less conducive water, a preferred exemplary embodiment, followed by refilling, gives the most uniform application of water and nutrients. Further, withdrawing substantially all of the less conducive water results in a period of emersion which is very stressful to some organisms which might otherwise colonize the pond, resulting in competition or consumption of the crop. For example, fish are intolerant of emersion. Moreover, withdrawing substantially all of the less conducive water gives the most complete elimination of unicellular algae from the growth medium, giving improved suppression of competition from unicellular algae.

The frequency of withdrawing and refilling depends on several factors, including the influence of irrigation on growth rate, the effect of irrigation on pH and salinity and the distribution of nutrients in irrigation water to the crop. In a preferred exemplary embodiment, ponds are drained completely and refilled at daily intervals. The draining and refilling interval may also be shorter than daily, e.g. twice daily. However, there is only small improvement in yield that probably does not justify the added expense of twice daily refilling. Growth of Enteromorpha is not maximal in growth medium that has been used for over 1 week, even with repeated nutrient addition. Because of this growth rate decline, the medium should be changed at least once a week. More frequent changes may be necessary if required for stress factor management or fertilization. For sites where water cost is low, daily water exchange is preferred. At sites where water cost is higher, it may be most economical to use less water, even if yields are somewhat diminished. Irrigation frequency is more important in the rapid growth phase than in the starch accumulation phase. Daily water exchange is still preferred in the starch accumulation phase where water cost is low.

Irrigation may occur at any time of the day or night. Care should be exercised that the crop does not become too dry during the period of emersion. Complete desiccation of the algae is lethal, and sublethal drying can result in reduced yield.

The water in accordance with the present invention is conducive to the growth of *Enteromorpha clathrata*. Conducive water preferably allows for a growth rate of at least 5 g dry weight per $m^2$-day to 40 g dry weight per $m^2$-per day. The conducive nature of the water is determined by its salinity, pH, nutrient content and possibly other factors. Preferably, conducive water has a pH between 7.5 and 9.5. Preferably, the conducive water has a salinity not exceeding 300 ppt. More preferably, conducive water has a salinity not exceeding 70 ppt, most preferably, a salinity of 35 ppt.

A pond is an enclosed body of water, of any depth and any topography. Predetermined water depth in the pond, in accordance with the present invention, should be as shallow as is consistent with rapid growth. The use of shallow ponds suppresses wave action without imposing restrictions on pond area. If the water is too shallow, it will suffer extreme variation in salinity, and will become depleted of nutrients more rapidly. Such problems can be overcome by more frequent medium exchange. Very shallow water require that the pond bottom be very flat, otherwise different areas of the pond will experience very different depths and management practices will be correct for only a fraction of the pond.

The ponds in which the *Enteromorpha clathrata* are grown preferably are shallower than conventional ponds. The advantages of shallow ponds are several: first, they are much less expensive to build than deep ponds. Because capital costs are a major factor in the economics of agriculture, including aquaculture and algal culture, minimization of capital costs is essential. Second, shallow ponds allow complete medium exchange on a regular basis without excessive water use. Third, shallow ponds exhibit very limited wave action, so floating algae retain an even distribution. Fourth, shallow ponds result in short distances between nutrient pools in pond water and the site of maximal photosynthesis at the water/air interface.

With deeper ponds, there may be the problem of movement of algae to one side, with resultant crowding and submergence, if there is high enough wind velocity. Water depth greater than about 10 cm allows excessive mat movement with wind forces. For this reason, a pond deeper than 20 cm is unworkable because the action of the wind and wind-generated waves will move the algae to one side of the pond and may submerge the algae, resulting in loss of productivity due to lack of air exposure. Ponds of greater than 10 cm of depth are successful with a thick mat.

Generally, the pond bottom must be flat enough to maintain approximately constant depth. Preferably, water depth is less than 20 cm and more than 1 cm. Most preferably, the depth is less than 7 cm and more than 3 cm.

As discussed above, the water is introduced into the pond through the use of pipes or channels. Even distribution of the fertilizer throughout the pond is essential to the high yield growth of the present invention. There is preferably an inlet and an outlet for the flow of water, each of which are preferably located at opposite sides of the pond. If the fertilizer is introduced by addition to the supply water and there is continuous, rather than intermittent water flow, then the algae located near the inlet will have sufficient nutrients. However, the water will become progressively depleted of nutrients as it flows to the outlet. Thus, the growth of the algae nearest the outlet will suffer from lower growth and yield. For this reason, the practice of replacing the less conducive water with the more conducive water on a regular basis in the present invention permits the nutrients to be more evenly spread throughout the pond. So long as flow rates of the water are high compared to the rate of nutrient uptake, algae more distant from the inlet will still be well fertilized. For this reason, the preferred time for refilling the more conducive water in the pond is less than two hours. Preferably, the amount of water used in the exchange is sufficient that phosphate application in the pond is both sufficient and non-toxic. This amount of water is preferably at least 20 liters per square meter.

Ponds are preferably situated so that water temperature is between 15° and 40° C., most preferably between 20° and 38° C. In temperate zones, Enteromorpha culture can only be carried out during the warmer parts of the year when temperature and light requirements are fulfilled.

IV. FERTILIZATION

In order to be grown economically, crops in general, and *Enteromorpha clathrata* in particular, must be fertilized. Fertilizer cost is a major variable expense for many crops, including, for example, corn. In the culture of *Enteromorpha clathrata*, fertilizer is actually more important than it is with other crops. The amount of nutrients, e.g. nitrogen and phosphorus, in sea water is low. This, combined with the low rate of water use of the present invention (discussed above), results in very slow growth of the algae if supplemental nutrients are not supplied. It is thus necessary to design fertilizer compositions and fertilization schedules that supply nutrients at a level sufficient for high productivity and at a level that is not toxic to the crop, in such a way that a large fraction of the fertilizer is taken up by the crop rather than being lost to the environment. Crops such as corn typically have a fertilizer use efficiency of between 30% and 70%. The *Enteromorpha clathrata* in the conditions of the present invention has a fertilizer use efficiency of over 90%, which is believed to be greater than any major crop.

If operated properly, cultures use essentially all fertilizer applied. Application of excess fertilizer should be avoided for several reasons. First, it adds to costs without producing any benefit. Second, excess fertilizer results in contamination of cultures by unicellular algae. Third, excess fertilization results in pollution of the environment. Fourth, prolonged excess fertilization will result in stimulation of zoospore production by Enteromorpha, resulting in lost productivity.

The brackish or saltwater in accordance with the present invention is supplemented with at least one fertilizer. Supplementation with a fertilizer can be accomplished by addition of nutrients to the supply water, or by spreading the nutrients over the pond, e.g., with a sprinkler or spreader. Fertilizer may be added at various intervals and concentrations as detailed below.

The fertilizer used in accordance with the present invention is preferably ammonia, ammonium, nitrate, urea or phosphate. These can be supplied in the form of ammonium chloride, ammonium sulfate, ammonium nitrate, sodium nitrate, potassium nitrate, calcium nitrate, urea, soluble organic forms of nitrogen, phosphoric acid, sodium phosphate, potassium phosphate, calcium phosphate. It may also be necessary to add micronutrients such as iron, molybdenum, zinc, or copper, or other micronutrients, depending on the micronutrient content of the supply water.

Preferably fertilizer is provided in quantities that can be utilized essentially completely by the crop. Enteromorpha can grow rapidly with protein content as low as 15%. For this reason, it is necessary to correctly match fertilization with growth rate. Underfertilization will result in a low protein product. Correct fertilization will result in high protein product. Overfertilization will result in failure of the algae to completely use the applied fertilizer, resulting in extra expense without additional production, and also in excessive growth of microalgae, resulting in diminished product quality. The correct level of fertilization depends on light and temperature conditions, and must be determined for a particular location.

The composition of the *Enteromorpha clathrata* is variable depending on the nutrients supplied. In particular, the protein content can range from 15% to 30%, while maintaining good yield. Lower protein content is associated with elevated starch content. Phosphate content can also vary, presumably because excess phosphate is stored, probably as polyphosphate. If phosphate is present at limiting levels, growth is restricted. Photosynthetic energy is put into starch accumulation, or if nitrogen is available, into protein accumulation. Protein levels do not seem to go much higher than 30% of dry weight. For use as animal feed (as discussed in more detail below) high protein levels are valuable, since high protein feeds are considerably more expensive than low protein, high energy feeds. In order to achieve high protein levels, a fertilizer is preferably used that provides sufficient phosphate for growth, but no extra, and sufficient nitrogen for accumulation of protein to 30% of dry weight. A fertilizer that accomplishes this provides nitrogen to phosphate in a molar ratio of 30:1.

The most preferred fertilizer composition is readily soluble, non-toxic, and least cost. A preferred fertilizer composition utilizes urea as a source of nitrogen with a final concentration in the pond of 1.5 mM (so 3.0 mM nitrogen), and phosphoric acid as a source of phosphate with a concentration in the pond of 0.1 mM. The preferred fertilizer of the present invention has a nitrogen to phosphate ratio of approximately between 10 and 40 to 1.

In addition to the major components, certain micronutrients are preferably included in the fertilizer, since they may not be readily present in sufficient levels in seawater. A micronutrient supplement that gives good results is 4.37 grams $FeCl_3$, 3.55 grams $MnSO_4$ 1.63 grams $ZnCl_2$, 0.2 grams $CuCl_2$, 0.03 grams $CoSO_4$, and 3.6 grams ammonium molybdate per 400 square meters applied with the nitrogen containing fertilizer, except for the ammonium molybdate, which is applied with the phosphate containing fertilizer. It should be noted that the presence of iron and either phosphate or molybdate in one fertilizer will result in precipitation, unless a chelation agent such as EDTA is included. The additional expense of the EDTA can most preferably be avoided by providing fertilizer as two fertilizer mixes, one containing urea and all micronutrients other that molybdate, and the other providing phosphate and molybdate.

For example, if it is desired to grow up cultures rapidly, e.g., for planting purposes, without particular regard to product composition or maximization of productivity, during rapid growth in good conditions, biomass increases by 15 grams dry weight per $m^2$-day. Between 1 and 5% of this dry weight is nitrogen, typically 3% or 0.45 grams per $m^2$. On a molar basis, this is about 30 mmoles/$m^2$-day. Assuming a water depth of 5 cm and fertilization two times per week, the concentration of N is preferably about 2.0 mM. In the rapid growth phase P is preferably about 0.3% of dry weight, hence the crop is preferably provided with about 0.45 grams P per $m^2$-day. On a molar basis, this is about 1.5 mmoles P per $m^2$-day. Assuming a water depth of 5 cm and fertilization two times per week, the concentration of P is preferably about 0.1 mM.

The upper limit on fertilizer concentration is determined by the toxicity of phosphate, which is safe at 0.1 mM, but is lethal at 0.5 mM and is preferably used at concentrations at or below 0.1 mM. Ammonia is quite toxic, to such a degree that its use is most preferably avoided, although concentrations up to 0.2 mM are acceptable. Other forms of nitrogen, nitrate and urea, do not exhibit significant toxicity.

Similarly, for a culture growing at very high yield intended for use as a high protein animal feed, biomass increases by about 25 grams dry weight per square meter per day, with 5% of dry weight as nitrogen, thus 1.25 grams nitrogen, or about 90 mmoles per square meter per day. Assuming water depth of 5 cm and fertilization 4 times per week, the concentration of N is preferably about 3.1 mM. P is preferably about 0.3% of dry weight, hence the crop is provided with about 0.075 grams P per day, or about 2.4 mmole per square meter per day. Assuming water depth of 5 cm and fertilization 4 times per week, the concentration of P is preferably about 0.08 mM, thus with an N/P ratio of between 30 and 40.

If the rate of uptake of the fertilizer is known, then it is possible to predict the time required for 90% uptake of applied fertilizer, given the initial concentration of nutrient and the current density of the crop. In general, once the crop has achieved a density of several grams fresh weight per liter, all of the nutrients supplied by a fertilizer with the maximum safe concentration of phosphate can be taken up within 24 hours. If fertilizer is provided daily at the highest safe concentration, sufficient nutrients are provided for productivity of over 40 grams dry weight per square meter per day. This corresponds to a yield of 146 tons dry weight per hectare per year. Because $CO_2$ diffusion rate, light and temperature conditions are expected to restrict yield, fertilizer concentration and/or fertilizer frequency should be held below the maximum permitted. In general, fertilizer is best applied at the maximum permitted concentration, although this is not necessary to success. Under normal conditions that otherwise allow yields of about 20 grams dry weight per square meter per day, fertilization three or four times per week is sufficient, with four times per week preferred if high protein content is desired. During crop establishment, greater care in fertilization is necessary, and it may be necessary to hold the fertilized water on the crop for several days to allow complete uptake. The required time depends on the density of the crop.

Fast growth of *Enteromorpha clathrata* is desirable when bringing new culture to a size sufficient to plant production ponds, or to obtain high productivity with low density cultures in the first stages of production. The lowest culture density preferred in large scale cultures is about 1 gram fresh weight per liter of medium. *Enteromorpha clathrata* exhibits increase in fresh weight of up to 100% per day in ideal conditions. A 10-fold increase per week, or about 40% increase per day, can easily be maintained continuously. Fast growing cultures must take up nutrients rapidly. For example, a culture that is increasing by 40% per day must, in order to maintain an N content of 3%, take up N at a rate of 0.4×0.03, or 1.2% of dry weight per day. Similarly, a culture that is increasing by 40% per day must, in order to maintain a P content of 0.5%, take up P at a rate of 0.4×0.005, or 0.2% of dry weight per day.

The efficacy of nutrient removal from the medium is lowest with the lowest culture density. At very low culture density of 1 gram fresh weight per square meter, biomass is low enough that fertilizer is not expected to be taken up for several days, regardless of the amount provided, and this should be taken into account in designing fertilization and irrigation regimes. In particular, because of the low fertilizer demand, it is sufficient to fertilize infrequently, for example, once or twice a week. Further, because of the low rate of uptake, fertilization at a low rate combined with frequent water exchange will result in wasted fertilizer and/or fertilizer levels too low for a nutrient uptake fast enough to sustain rapid growth. The period of time required for 90% uptake of nutrients by a 1 gram fresh weight per liter density culture is 2 to 3 days, so such cultures are preferably fertilized and irrigated at most twice per week.

Fertilization need not be done with every water exchange. Enteromorpha is capable of taking up excess nutrients and storing them for future growth, so fertilization can occur at greater levels and longer intervals. For example, cultures can be fertilized every two days with twice the concentration of nutrients specified above. Excessive concentrations of certain nutrients, such as ammonia (which is inhibitory at 2 mM), may be harmful. Forms of nutrients that are utilized more slowly, such as urea, will not be used efficiently if given in great excess. Ideally, if intermittent fertilization is done, nutrient uptake is measured to assure efficient use of added fertilizer.

Fertilizer additions need not be identical in composition from time to time. In particular, N and P can be provided on different schedules, according to the uptake rates and storage capacities for the individual nutrients. For example, P can be provided as described above, and N at twice the normal concentration, but given half as frequently as P. The advantage of intermittent fertilization or alternate fertilization is that the growth of the algae is limited by the storage of nutrients from one day to the next. This tends to limit algae to a certain percentage increase per day, so unwanted unicellular algae with very high potential relative growth rates are limited in their growth, but seaweeds with lower percentage growth rates and larger biomass are not, so contamination of cultures by unicellular species is minimized. The influence of nutrient availability on species composition has been studied in ecological circumstances related to the conditions in the ponds of this invention [24].

V. PLANTING AND HARVESTING

Planting of ponds is accomplished by introducing Enteromorpha into the ponds, either from another pond already in production, or from a pond dedicated to the growth of starter cultures for other ponds. The size of the inoculum depends mainly on economic concerns. The smaller the inoculum, the longer it will be before the pond is ready for harvest. In the first phase of growth, algae are permitted to grow rapidly without regard to productivity or composition. In the second phase, algae are grown at high productivity, and with fertilization designed to result in the desired composition. In the first phase of growth, sufficient N, P, and other nutrients are provided for rapid growth, but at levels low enough that complete removal of nutrients from the growth medium occurs within a few days. This first phase continues until a sufficient fresh weight of algae is developed, typically about 2 kg/m$^2$. In the second phase, nutrients are limited. In one preferred embodiment, P availability limits growth, but sufficient N is provided to satisfy the ability of the algae to take up and store N. In this phase, starch and protein are stored by the algae with modest increase in fresh weight but approximately tripling the dry weight, i.e., the dry weight to fresh weight ratio increases. This results in a product that is high in starch and protein, giving it enhanced value as feed or chemical feedstock or source of starch or protein compared to algae grown according to the methods of the prior art. In a rapidly growing culture, the second phase lasts 1 to 2 weeks.

Once culture density rises, productivity is limited by light availability and $CO_2$ diffusion, and the percent growth rate falls. In this stage of crop development, much lower rates of nutrient uptake per gram of tissue are required. The total accumulation of dry matter is maximal at this stage, however, so the amount of nutrients applied to the crop is also maximal. Any possible toxic effects of nutrients are therefore most critical at this stage.

There is a relationship between the culture density of the Enteromorpha clathrata and yield. Yield is limited by growth rate at low culture density. When culture density is high enough, yield becomes limited by other factors such as light or nutrient availability. Cultures are preferably not operated very far above the point at which yield becomes maximal, since average growth rate falls inversely with the amount of standing biomass, hence the harvested crop will have a greater average age and be more likely to contain extraneous organisms and hence be of a lower quality.

At the end of the second phase, the algae is harvested, with yields of about 600 g dry weight/m$^2$, or about 6 tons dry weight/ha. After harvesting, the pond is restocked with Enteromorpha and the cycle is repeated. Restocking can be done by recycling a portion of the harvested algae, or from nursery pond.

Alternatively, only a portion of the crop may be harvested, leaving a portion in the pond. For example, half of the crop can be taken, and half left in the pond. The remaining portion can then be spread, e.g., by using tools such as rakes, or by using a stream of seawater, or by pumping water through the pond.

A free-floating culture unattached to the bottom is the preferred method, but it is possible to grow attached cultures as well. In order to harvest, the algae must be freed from the bottom, e.g., by dragging a rope or chain through the pond. Attached algae will develop in time, whether desired or not, but the presence of a floating mat inhibits the growth of bottom attached algae. If bottom attachment is desired, it is best achieved by complete harvest of the crop, followed by rapid regrowth of the remaining attached algae.

The two phase growth cycle can optionally be replaced by a gradual shift in conditions, or by a single phase with constant nutrient conditions. The two phase growth cycle gives a better control of product composition than a single phase. Further, in general, a free-floating crop is preferred.

Harvesting is preferably accomplished by floating the algae to an edge of the pond, using water flows, or by dragging a rope or cable stretched or floated across the pond along the length of the pond, or by pushing the algae by hand or with machines and removing it from the water using screens or pitchforks or equipment designed for the purpose. Floatation can be aided by temporarily increasing the water depth to accommodate the large mass of algae. The flotation of the mat in deeper water can be used to advantage for harvesting. The pond can be filled with water to a sufficient depth to render the mat mobile, typically about 10 cm. Water can then be pumped through the pond, entering the supply end and drained by an overflow at the drain end. Alternatively, water under pressure may be directed at the surface of the mat, e.g., with a hose with a nozzle attached, so that the action of the stream of water causes the Enteromorpha mat to move to the harvest point. The resultant water flow carries the mat to the drain end of the pond, where it can be picked up and loaded into trucks or wagons for transport, or otherwise processed. The advantage of harvesting in this manner is that it is not necessary to drive equipment through the ponds to pick up the crop. The cost of operating and maintaining harvesting equipment is replaced by slightly increased use of the seawater pump, resulting in low harvest costs.

VI. SPECIES CONTROL

In growing Enteromorpha clathrata according to the present invention, it is important that the growth of microalgae or unicellular algae be controlled. Microalgae can grow very rapidly. They do not develop significant biomass, but they can degrade the quality of the crop. The microalgae may be controlled by the fertilization scheduling. For instance, the complete uptake of the nutrients by the algae is one method for controlling the growth of the microalgae. Fertilization at maximal rates followed by irrigation without fertilizer permits only intermittent growth of microalgae. Irrigation tends to wash out microalgae. For this reason, the preferred fertilization regime utilizes fertilization at the maximal acceptable concentration, interspersed with irrigation at a frequency sufficient to prevent excess water loss due to evaporation or leakage, and at a frequency sufficient to wash out any microalgae which may grow. For typical near shore conditions, irrigation can be done daily, with four fertilizations per week.

In addition to fertilization scheduling there are several other strategies for species control in seaweed cultures. First, the stresses of shallow water culture of the present invention will eliminate most potential competitors and many potential consumers. Second, periodic drainage results in some drying and air exposure of the cultures. This eliminates additional competitors and most potential consumers, such as fish and many invertebrates. Drained cultures can be washed with a water spray to reduce populations of unicellular algae. The water spray may be seawater or fresh water, especially for those strains that are fresh water tolerant, fresh water can act to eliminate many undesired organisms. Antibiotics or toxics may be useful in species control. For example, Enteromorpha is tolerant of many antibiotics, so these could be used to eliminate unwanted organisms. The particular strains of Enteromorpha that are used are tolerant of high copper levels, unlike most algae, so copper treatment can be used to eliminate contaminating algae. Some chemical agents used in agriculture are known to be highly toxic to fish and invertebrates, and these may prove useful in controlling organisms that may consume algae. Strategies of species control will depend strongly on the nature of the invading species, and the tolerance to potential control measures of the algae grown as a crop.

VII. POST-HARVESTING PROCESSING

After collection, the crop is preferably rinsed with fresh water to reduce the amount of salt in the crop. The principal costs associated with this step are for the investment in tanks or other vessels required for desalting. As such, desalting cost is largely determined by the amount of time required for desalting, since this determines the efficiency with which capital investments are used. Because *Enteromorpha clathrata* is composed of hollow tubes that are only a single cell thick, the diffusion distance is very short. Desalting requires less than fifteen minutes exposure to fresh water, resulting in low desalting cost. This low cost desalting is a fortuitous consequence of the structure of *Enteromorpha clathrata*.

After desalinization, the algae is drained, pressed, or rolled to dry to some degree before being collected for processing or storage. Alternatively, the algae may be allowed to dry in the drained pond. Once partly dried, the algae can be handled in the same way and with the same equipment as is used for cut hay. In dry climates where complete drying is possible, complete drying should be avoided until it is desired to powder the algae.

Drying cost is determined mainly by two factors: primarily the capital investment cost and secondarily the energy cost. Capital investment cost is strongly determined by the speed of drying. Enteromorpha is readily dried, as a consequence of its thin structure combined with the easy air penetration of the filamentous mat. In a suitable climate, it can be completely dried in less than 48 hours without supplemental heat or special equipment. Where climate is not suitable, supplemental heat and special structures may be required. Using supplemental heat, Enteromorpha can be completely dried in as little as one hour, much faster than other crops. Thus, for Enteromorpha, unlike other crops, the cost of drying is determined mainly by the cost of supplemental heat, because capital costs are so low. In dry climates, drying is therefore most preferably accomplished without supplemental heat. Where humidity is too high, preliminary drying without supplemental heat is preferably followed by final drying step with supplemental heat. When supplemental heat is used, temperatures over 60° C. should be avoided, especially if xanthophyll content in the product is desired, as discussed in more detail below.

Drying should proceed until the crop has reached about 10% water content. At the correct water content, the crop is readily shattered, so it is easily milled. The crop can be stored in the dry state in closed containers in the dark for periods of at least several months without detectable loss in quality.

VIII. FEED USE

Also presented in accordance with the present invention is a method of producing feed involving growing *Enteromorpha clathrata* according to the above-described method and harvesting the *Enteromorpha clathrata* from the pond and processing the harvested *Enteromorpha clathrata* to produce feed. Processing of the harvested *Enteromorpha clathrata* may be minimal, i.e., the algae may be fed fresh. Preferably, the algae is dried to a water content of about 20% (w/w), in which condition the algae is preserved against decay but is easily handled without powdering. Alternatively, the algae can be partially dried to a water content of less than 50%, and pressed, extruded, or rolled to form pellets or sheets. This product should be further dried if necessary to achieve a water content of less than 20%. A milling step may be used before pressing, extruding or rolling to improve formability of the product. Pelletization gives a convenient form for use as feed.

Alternatively, the algae is preferably dried to a water content of 15% or less so that it is readily powdered. The powdered form is convenient for addition to chicken feed, or other feeds provided in a powdered form. Fine milling also improves digestibility of feeds in non-ruminants, such as chickens and pigs. For production of powdered algae especially in humid regions, it may be necessary to dry algae collected in an enclosed storage space using a flow of air that has been heated or dehumidified. Methods now used for drying grain would be applicable. The powdered form may be granulated or made into pellets or may be used as an ingredient in feed formulations. Enteromorpha powder may be further processed to result in enrichment of certain fractions. For example, a fraction depleted in cell wall fraction could be used as a starch and protein rich feed. A fraction additionally depleted in starch could be used as a protein source. Fractionation can be done by, for example the method of [4].

As an ingredient in animal feed in general, Enteromorpha has the virtue of being high in protein. Because protein is at present substantially more expensive than the energy component of feed, a crop as high in protein as possible is preferably produced. As discussed below, when grown with sufficient nutrients, Enteromorpha is about 30% protein. This is much higher than is typical of terrestrial crops, approximately comparable to the protein levels found in soybeans. Because Enteromorpha has far higher yields than any terrestrial crop, the protein production per hectare for Enteromorpha is about 10-fold higher than alfalfa, its closest competitor, and far higher than corn, soybean, or wheat. Protein content is strongly influenced by nutrient availability.

The *Enteromorpha clathrata* grown according to the method of the present invention in one preferred embodiment is used as a nutritious feed for farm animals such as chickens, cattle, goats, sheep, horses, and pigs. As an ingredient in chicken feed, Enteromorpha has the virtue of containing high levels of xanthophylls, which are important in providing color to egg yolks, and which contribute to the yellow color of the skin of broiler chickens. The principal xanthophyll of Enteromorpha is lutein, which is also the principal xanthophyll of the leaves of terrestrial plants. The xanthophyll content of Enteromorpha declines with nutrient deficiency, but otherwise is not strongly dependent on culture conditions.

When grown and processed as described herein, Enteromorpha has a composition similar to high protein alfalfa leaf meal, but with somewhat higher protein and carotenoid levels. Alfalfa leaf meal or hay is used as a feed component for many animals, including cattle, pigs, chickens, goats, sheep and horses.

IX. EXAMPLES

EXAMPLE 1: RAPID GROWTH OF ENTEROMORPHA IN FLOATING CULTURE

1. BATCH CULTURES

*Enteromorpha clathrata* cv. Berkeley was grown in the laboratory under conditions similar to those expected during production in the field. Light was provided by a 1000 watt metal halide lamp suspended above the plants, giving PAR of 400 microeinsteins/m$^2$-sec. Water temperature varied from room temperature at night, 24° C., to a daytime maximum of 33° C. Cultures were open to the air. Evaporation was about 0.5 cm/day. The pH was not controlled, but varied from an initial value of 8.0 to a maximum of 10.1. Cultures in high light were grown in sea water supplemented with 0.3 mM Urea, 0.12 mM $Na_2HPO_4$, 10 microgram/l vitamin B12 and a micronutrient supplement to give final additional concentrations of $10^{-6}$ M molybdate, $10^{-7}$M copper, $10^{-6}$M manganese, $10^{-7}$M zinc, $5\times10^{-8}$M cobalt, $5\times10^{-4}$M borate and $10^{-6}$M Fe-EDTA. These cultures had dry weight accumulation rates of about 28 g/m$^2$ day, with daily medium exchange at a rate of 50 l/m$^2$. Assuming similar daily yields were maintained for one year, this would correspond to dry weight yields of 100 tons per hectare year. This is somewhat lower than maximum growth rates reported for the most productive algal systems (about 150 tons per hectare year), but it is achieved in low cost conditions. Water use rates are almost 100 times smaller than in the high yield cultures, and pond construction and operation is much simpler. Even though yields may fall a little short of the highest observed yields, they are still greater than any terrestrial crop and far higher than most.

2. STEADY STATE CULTURES

In a separate experiment, cultures of *Enteromorpha clathrata* cv. Berkeley were maintained in conditions sufficient to give continuous moderate vegetative growth. Such conditions could be used for production or as nursery cultures for stocking production ponds. Cultures were maintained in containers drained from the bottom, drained at 5 AM, refilled at 6 AM to a depth of 5 cm. Lighting was provided by two metal halide lamps (1000W each, on at 6 AM, off at 10 PM), providing a total illumination of between 400 and 500 $\mu$Einsteins/m$^2$-sec to an experimental area of 3 feet by 2 feet. The culture medium was Instant Ocean supplemented with 0.3 mM urea and 0.03 mM phosphate, 0.3 $\mu$M iron and with the initial pH adjusted to 8.0. Cultures were divided in ½ once per week, and one half was discarded. Growth was approximately constant for 12 weeks, resulting in the algae doubling once per week, being cut in half, and doubling in the following week. The fresh weight of cultures was determined, and the dry weight ratio/fresh weight ratio determined on a subsample. The dry weight/fresh weight ratio was approximately 0.2. Fresh weight increased form 1 to 2 kg/m$^2$ in one week, so dry weight increased from 200 to 400 grams/m$^2$-week, or about 28 g/m$^2$-day. If this yield is maintained for 365 days a year, it corresponds to yields of about 100 tons dry weight/ha-yr. If this culture were used as a nursery culture, it could stock two ponds its size every week, or about 5 ponds on a continuous basis.

3. SUBMERGED CULTURES

Experiments were designed to test whether Enteromorpha absorbs carbon dioxide from the air. Using 50 l/m$^2$-day medium exchange, almost 30 g/m$^2$-day dry weight accumulation was observed. Medium exchange provides sufficient inorganic carbon for 3 g carbohydrate/m$^2$ day, if it is all used. The great majority of carbon must be from atmospheric $CO_2$. The rate of $CO_2$ absorption into pH 10 seawater is sufficient for the accumulation of approximately 0.66 g carbohydrate dry weight/m$^2$ day. The great majority of $CO_2$ absorption must occur directly into the emergent part of the floating algal mat. If $CO_2$ absorption from the air is required for high productivity, submerged Enteromorpha, like other non-floating algae, should exhibit slow dry matter accumulation. To test this, tissue samples were placed in medium in magenta boxes and weighed down with a glass slide placed on end. The filaments were not compressed or crowded, but were held at least a centimeter below the water surface. Algae when floating increased in dry weight by over 25 g/m$^2$ day, but when submerged increased in dry weight by less than 5 g. This result is consistent with the idea that most carbon uptake by the floating mat is from the air.

EFFECT OF STRESS ON PRODUCTIVITY AND COMPOSITION

EFFECT OF PHOSPHATE DEPRIVATION ON STARCH CONTENT

Samples of Enteromorpha cv. Berkeley were grown as batch cultures for a period of 10 days, and then grown in a similar fashion but with ⅒ the amount of phosphate. After a period of 2 weeks, the starch content was determined. Starch content of samples varied between 50 and 70% dry weight.

EFFECT OF ELEVATED SALINITY ON DRY WEIGHT ACCUMULATION

The effect of elevated salinity on productivity was determined in dense culture conditions. Average dry weight increases observed in 1, 1.5, 2 and 2.5× seawater concentration are shown in Table 1. Increase in dry weight is not inhibited even in the 2.5× seawater. Tissues from 2 and 2.5× treatments show increased starch accumulation.

TABLE 1

| EFFECT ON SALINITY ON PRODUCTIVITY OF *E. CLATHRATA* CV. BERKELEY | | | | |
| --- | --- | --- | --- | --- |
| SALINITY (PPT) | 35 | 52 | 70 | 87 |
| CHANGE IN DRY WEIGHT (g/m$^2$-day) | 27 | 29 | 28 | 33 |

EFFECT OF ELEVATED PH ON DRY WEIGHT ACCUMULATION

Cultures of *Enteromorpha clathrata* cv. Berkeley were grown as described for batch cultures, except that 10 mM TRIS buffer was used to control the pH. Table 2 shows average one day increases in dry weight for cultures at pH 8, 9 and 10. There is no significant difference between the different pHs. Cultures maintained in pH 9 and 10 exhibit reduced elongation. The increase in dry weight appears to be due at least in part to starch accumulation: IKI straining shows numerous large starch grains in the high pH grown tissue (data not shown). Only small starch grains are visible in the pH 8 grown tissue.

TABLE 2

| EFFECT OF pH ON PRODUCTIVITY OF *E. CLATHRATA* CV. BERKELEY | | | |
| --- | --- | --- | --- |
| pH | 8 | 9 | 10 |
| CHANGE IN DRY WEIGHT (g/m$^2$-day) | 23 | 26 | 28 |

UPTAKE OF NUTRIENTS BY ENTEROMORPHA

The uptake of nutrients is well known in algae, including Enteromorpha [35], including the uptake of phosphorus and nitrogen. The instantly disclosed cultivar is no exception. For example, Enteromorpha was cultured as described above for batch culture with an initial inoculum of about 1 g fresh weight in 200 ml of medium. Phosphate depletion of the medium and phosphate uptake by the tissue were measured. Phosphate was taken up at a rate of about 2 μmoles/g fresh weight-hr from a 40 μM Solution, resulting in doubling of tissue phosphate levels in about 6 hours. In a dense culture, enough phosphate can be taken up in 6 hours for about 1 week of growth. Ammonia was taken up at a rate of about 100 μmoles/g fresh weight—hr from a 1.5 mM solution. A 5 cm deep solution is depleted of ammonia within 6 hours at a culture density of 300 g/m$^2$.

EXAMPLE 2: EFFECTS OF FERTILIZERS ON PRODUCTIVITY OF *E. CLATHRATA* CV. BERKELEY

One week prior to experimentation, and during experiments, *Enteromorpha clathrata* cv. Berkeley plants were grown in a greenhouse without shading or artificial lights. Air temperature varied from 20° to 25° C. Experiments conducted in the lab were carried out under metal halide lights which provided 300 mE m$^{-2}$ s$^{-1}$. Plant material was grown under artificial light for one week before experimentation. Air temperature was 21° to 24° C. Media were Instant Ocean supplemented with nitrogen as urea, nitrate or ammonia as noted in the text, phosphate as monobasic sodium phosphate, and micronutrients. Except as noted, cultures were not buffered or stirred, resulting in oxygen supersaturation and pH of about 10 after 2 to 3 hours of photosynthesis. Where noted for composition determinations, plant material was grown in small ponds with automatic irrigation designed to model agricultural practice. Ponds were drained to a depth of 1 cm beginning at 8 a.m., refilled with instant ocean from 9 a.m. to 10 a.m. Instant Ocean was fertilized with separate urea and phosphate fertilizer streams at the fill point. Urea fertilizer was supplemented with iron and other cationic micronutrients. Phosphate was supplemented with molybdate. Ponds were housed in a greenhouse with temperature maintained between 20° and 25° C. Ponds were planted at a rate of 500 gfw (grams fresh weight) m$^{-2}$, grown for 4 weeks and harvested. Productivity ranged from 250 to 400 gdw (grams dry weight) m$^{-2}$ harvest$^{-1}$, depending on fertilization rate and time of year.

The phosphate content of *Enteromorpha clathrata* varies with growth conditions. In phosphate deficient conditions (N/P molar ratio=50), phosphate content was as low as 0.036% of dry weight. When grown with limited nitrogen (100 micromolar phosphate, N/P molar ratio=1), the phosphate content was between 0.38 and 0.79%, Table 1.

TABLE 3

|  | normal growth | p-deficient | n-deficient |
|---|---|---|---|
| phosphate | 0.43 (0.26–0.60) | 0.12 (0.036–0.26) | 0.592 (0.38–0.79) |
| protein | 25.7 (19.2–31.9) | n.d. | 12.5 (11.5–13.1) |

TABLE 3. Phosphate and protein composition of Enteromorpha. Data are averages of four or more determinations. Ranges are shown in parentheses. Data are % of dry weight. P-deficient tissue was grown with reduced phosphate so N/P =50 for 4 weeks. N-deficient tissue was grown with reduced nitrogen, so N/P=1 for 4 weeks. N.d.: not determined.

In fast growth conditions ("normal growth" in Table 3), 10-fold growth per week, phosphate content averaged 0.43%. For the early stages of culture in which growth is rapid, our target phosphate concentration is 0.4%, giving a target for uptake of 0.12 g phosphorus m$^{-2}$ day$^{-1}$, for a culture growing at the rate of 30 g dry weight m$^{-2}$ day$^{-1}$. This requires an initial phosphate concentration of at least 78 μM. For rapid growth (=40%/day) of starter cultures, phosphate uptake must occur at a rate of 0.004×0.4=1.6 mg phosphorus gdw$^{-1}$ day$^{-1}$, or 2.2 μmoles P gdw$^{-1}$ hour$^{-1}$, or about 0.22 μmoles P gfw$^{-1}$ hour$^{-1}$.

PHOSPHATE UPTAKE RATE

In laboratory experiments, phosphate uptake rate was proportional to concentration for initial concentrations of 100 and 30 micromolar. Except as noted below, linear (exponential decay) kinetics gave a good fit to the data. The time course of phosphate depletion is shown in FIG. 1 for several experiments with initial phosphate concentration of 30 μM.

Experiments with initial concentrations of 100 μM had similar kinetics, with the same ½ time of depletion [data not shown]. The initial uptake rate with initial phosphate concentration of 100 μM was 50 μmoles gdw$^{-1}$ hour$^{-1}$, or about 5 μmoles gfw$^{-1}$ hour$^{-1}$. Greenhouse experiments gave very similar uptake rates. Little or no phosphate uptake occurred in the dark. The time course of phosphate depletion can be described by the equation:

$$C = C_i \exp(-k_1 Dt)$$

where C is the concentration at time t, $C_i$ is the initial concentration, e is the base of the natural logarithms, $k_1$ is a rate constant with units of liter gfw$^{-1}$, D is the culture density with units of gfw liter$^{-1}$, and t is the elapsed time in hours. The observed rate constant of 0.05 liter gfw$^{-1}$ hour$^{-1}$ indicates that phosphate uptake by a culture of density 1 gram fresh weight per liter would have an uptake ½ time of 13.5 hours and require 46 daylight hours for 90% uptake efficiency.

Figure 2:
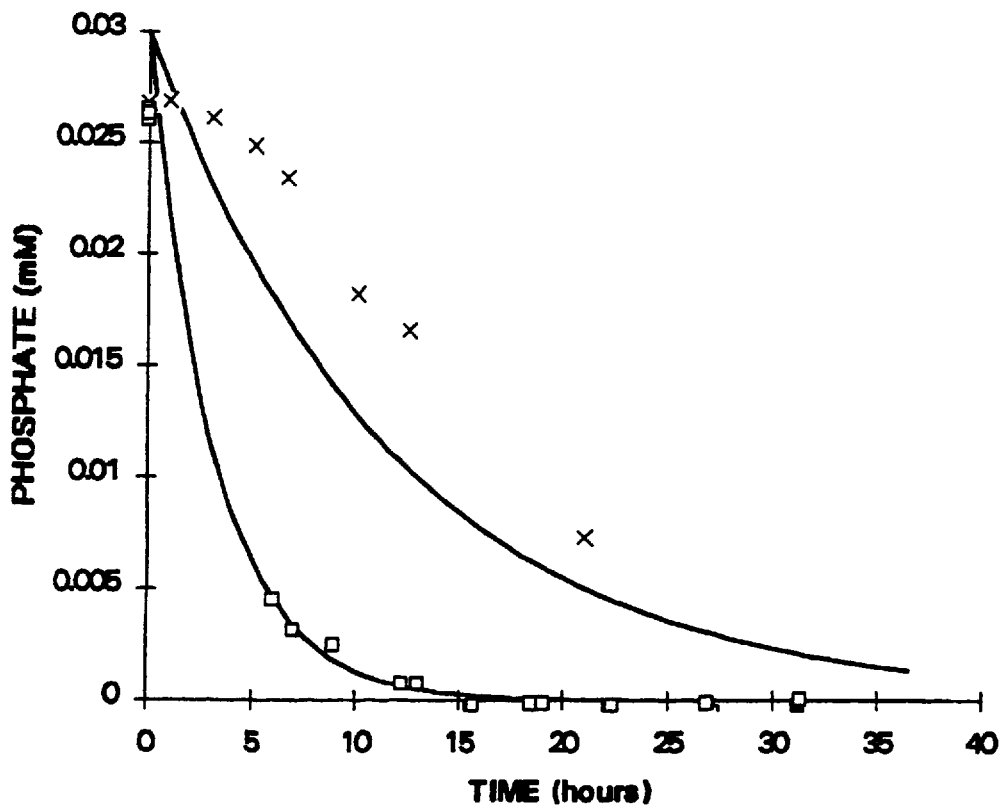
FIG. 2 is a graph showing the phosphate depletion time course with nutrient deficient tissue. Data points are (X) from an experiment with nitrogen deficient tissue and (□) from three independent experiments using phosphate deficient tissue. The upper line shows the expected time course of phosphate depletion assuming a rate constant of 0.050 liter $gfw^{-1}$ $h^{-1}$, to facilitate comparison with FIG. 1. The lower line shows the expected time course of phosphate depletion assuming a rate constant of 0.175 liter $gfw^{-1}$ $h^{-1}$ Cultures were illuminated during the entire course of the experiment.

The uptake rate of phosphorus was sensitive to the previous history of the tissue tested. FIG. 2 shows data from three experiments in which one half gram fresh weight of tissue previously grown in low phosphate medium removed essentially all of the phosphate from 300 ml of a 30 micromolar solution in about 12 hours, with a rate constant of 0.175 liter gfw$^{-1}$ hour$^{-1}$.

Experiments with initial phosphate concentration of 100 μM gave similar results [data not shown]. Tissue previously grown in low nitrogen medium showed a lag period of about 5 hours, followed by uptake with a rate constant similar to the unstressed control. FIG. 2 shows one such experiment. Other experiments with different planting densities had similar lag times and subsequent ½ times.

Because phosphate is capable of forming insoluble compounds, especially at high pH, these experiments were carried out in buffered conditions to maintain a pH of 8. Experiments in which the pH was allowed to rise gave very similar results [data not shown]. Acid wash of the walls of the magenta box in which culture was carried out contained only 1 to 3% of total initial phosphate. In general, phosphate was completely removed from the medium and about 80% of it could be determined in the tissue. The unaccountable phosphate was not present on the walls or in a detectable form in the medium. Ashing of dried medium did not reveal any otherwise undetectable phosphate. Medium phosphate does not decline in the absence of plant tissue.

There is no evidence of toxicity at a concentration of 100 micromolar. Toxicity was observed at 500 μM and 1 mM. These concentrations of phosphate resulted in visible precipitation on the algal filaments, and also in partial bleaching of the algae after 24 hours.

NITROGEN UPTAKE

PROTEIN CONTENT OF TISSUES. Protein content varied depending on growth conditions, from about 12% in nitrogen deficient medium (N/P molar ratio=1, N as 0.075 mM urea), to over 30% in nitrogen sufficient medium (N/P molar ratio=12, N as 0.75 mM urea). Nitrogen sufficient conditions ("normal growth" in Table 1) were established using small ponds with automatic irrigation designed to model agricultural practice. Taking 25% protein as our target, and assuming that tissue N is protein/6.25 or 4%, the target uptake rate is 1.2 g N m$^{-2}$ day$^{-1}$ for a culture growing at 30 gdw m$^{-2}$ day$^{-1}$. This requires an initial nitrogen concentration of 1.71 mM for a 5 cm deep culture. For rapid growth (=40%/day) of starter cultures, nitrogen uptake must occur at a rate of 0.04×0.4=16 mg nitrogen gdw$^{-1}$ day$^{-1}$, or 1.142 $\mu$moles N gdw$^{-1}$ day$^{-1}$, or about 4.8 $\mu$moles N gfw$^{-1}$ hours$^{-1}$.

Figure 3:
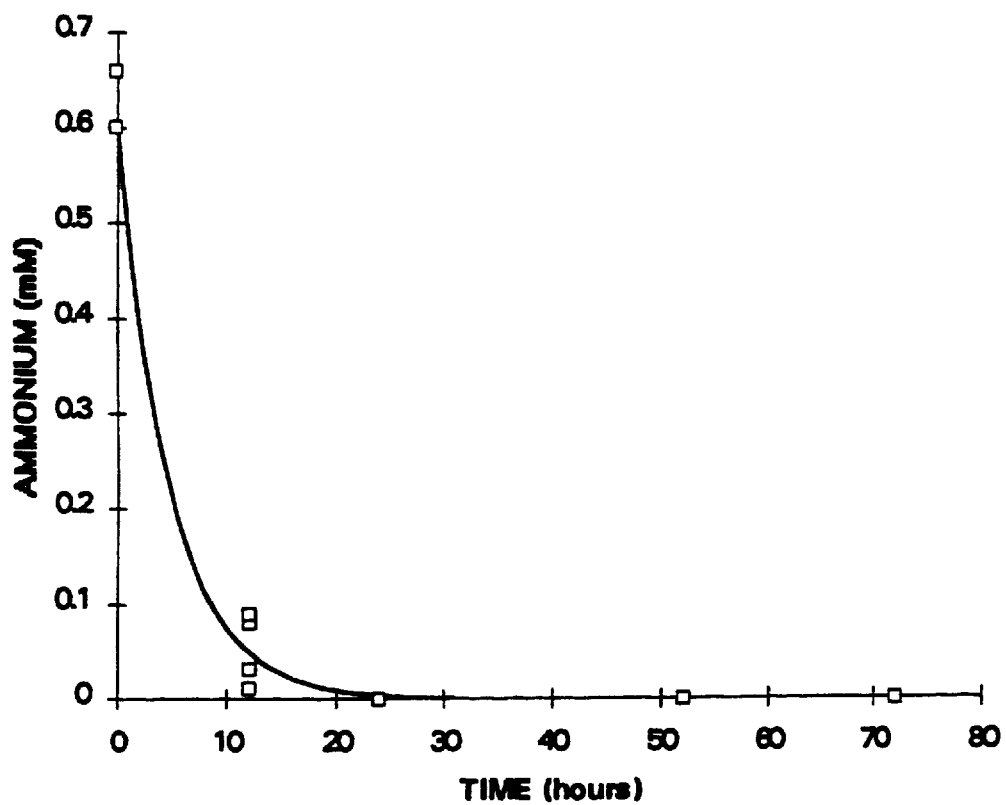
FIG. 3 is a graph showing the Ammonium depletion time course. Data points are from 4 independent experiments, using 0.5 gfw in 300 ml of medium. The solid line shows the expected time course of ammonium depletion assuming a rate constant of 0.115 liter $gfw^{-1}$ $h^{-1}$.

AMMONIUM. In laboratory experiments, ammonium uptake rate was proportional to concentration for initial concentrations of 1500 and 600 micromolar. Kinetics appeared to be linear, i.e., depletion from the solution was reasonably described by an exponential decay. In greenhouse experiments, one half gram of tissue took up about 90% of the ammonium from 300 ml of 300 $\mu$M ammonium sulfate (600 $\mu$M ammonium ion) solution in 12 hours, FIG. 3.

The initial uptake rate was about 69 $\mu$moles gfw$^{-1}$ hour$^{-1}$. The time course of ammonium depletion can be described by the equation given above for phosphate but with a rate constant of 0.115 liters gfw$^{-1}$ hour$^{-1}$. The observed rate constant of 0.115 liter gfw$^{-1}$ hour$^{-1}$ indicates an uptake ½ time of 6 hours and 94% removal in 24 hours for a 1 gram per liter culture density for any amount of ammonia in a range where the linear decay kinetics are valid. For example, with an initial concentration of 0.1 mM, 94 $\mu$moles of N could be taken up as ammonium in 24 hours by 1 gram fresh weight of tissue in 1 liter of medium. The rate constant observed in laboratory experiments was not significantly different from that seen in greenhouse experiments. These data were obtained in buffered solutions, to prevent the volatilization of ammonia at high pH. At pH less than 8.5, ammonia loss was negligible compared to the rate of uptake by the tissue [data not shown].

In growth chamber experiments, ammonium caused death within 1 week a 1 mM. In greenhouse experiments, ammonia at 0.6 mM resulted in a 30% inhibition of fresh weight accumulation in a one week period compared to plants grown in urea, in nitrate and in a combination of urea and nitrate, all with 0.6 mM N. Growth in the greenhouse was normal in 0.2 $\mu$moles ammonium.

Figure 4:
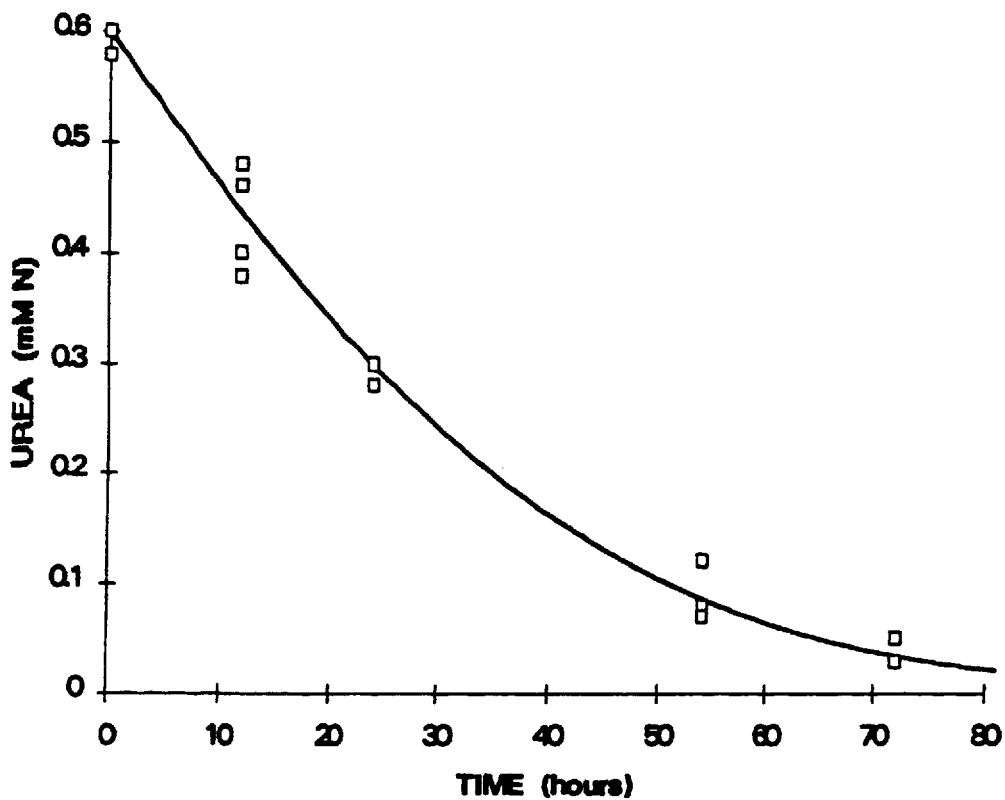
FIG. 4 is a graph showing the urea depletion time course. Data points are from four independent experiments, using 0.5 gfw in 300 ml of medium. The solid line shows the expected time course of urea depletion assuming rate constants of k1, 0.015 mmol N $gfw^{-1}$ $h^{-1}$ and k2, 0.45 mM.

UREA. Laboratory experiments showed no significant difference in initial urea uptake rate at concentrations of 0.35 mM (so 0.7 mM N) and 0.1 mM (so 0.2 mM N). In greenhouse experiments, one half gram fresh weight of tissue removed about 50% of the urea from 300 ml of 0.3 mM solution of urea (so 0.6 mM of N) in 24 hours, FIG. 4.

The initial uptake rate was 190 mmole N gfw$^{-1}$ day$^{-1}$, or about 8 mmole N gfw$^{-1}$ hour$^{-1}$. The rate of depletion of urea from the medium can be described by the equation:

$$\frac{dC}{dt} = \frac{-k_1 D}{1 + k_2/C}$$

where dC/dt is the rate of change of the concentration of urea in mM N hour$^{-1}$, $k_1$ is a rate constant with units of mmol N gfw$^{-1}$ hour$^{-1}$, D is the culture density in gfw liter$^{-1}$, $k_2$ is a rate constant in mM, and C is the concentration of urea at time t in mM N. The observed rate constants were $k_1$, 0.015 mmole N gfw$^{-1}$ hour$^{-1}$; $k_2$, (½ saturation) 0.45 mM N. Uptake rate was not significantly different in laboratory and greenhouse experiments. These rate constants indicate that an initial concentration of 0.3 mM urea will be 90% utilized by a 1 gfw liter$^{-1}$ culture in about 60 hours, and an initial concentration of 0.05 mM urea will be 90% utilized by a 1 gram fresh weight per liter culture in about 45 hours.

No toxicity at a concentration of 2 mM urea was observed.

Figure 5:
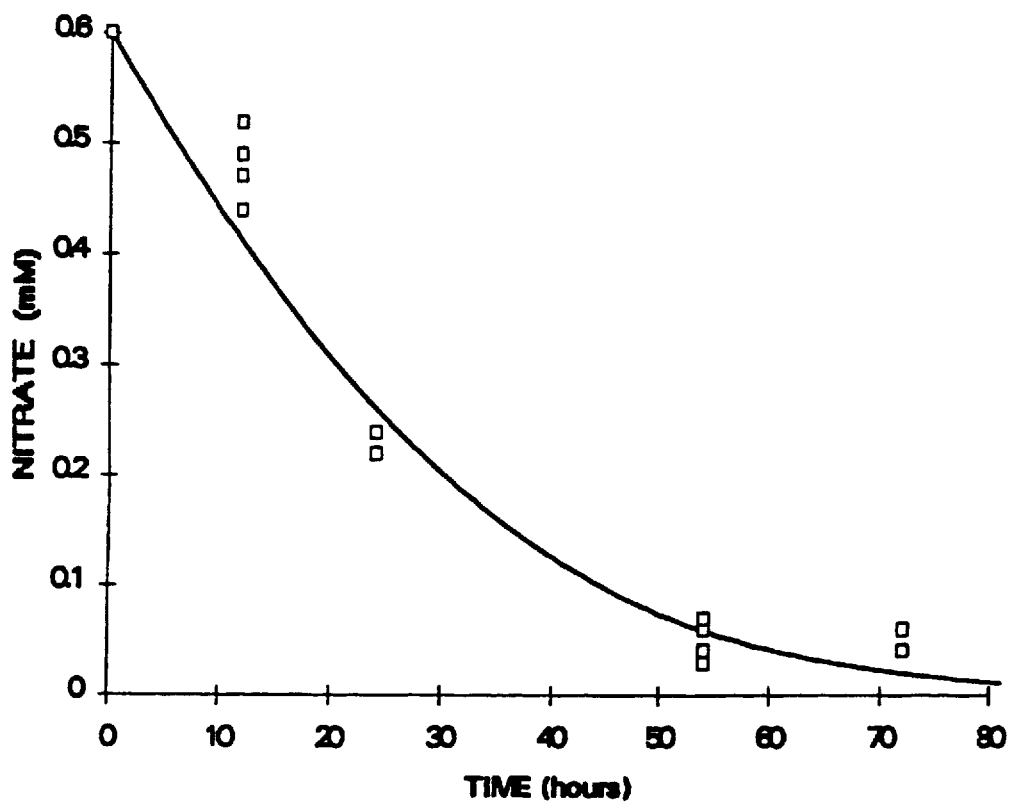
FIG. 5 is a graph showing nitrate depletion time course. Data points are from four independent experiments. The solid line shows the expected time course of nitrate depletion assuming rate constants of k1, 0.018 mmol $gfw^{-1}$ $hour^{-1}$ and k2, 0.5 mM.

NITRATE. Laboratory experiments showed no significant difference between uptake rates at initial nitrate concentrations of 1.5 and 0.6 mM. In greenhouse experiments, one half gram fresh weight of tissue removed over 60% of the nitrate from 300 ml of 0.6 mM solution of sodium nitrate (so 0.6 mM of N) in 24 hours, FIG. 5.

The initial uptake rate was about 220 $\mu$moles gfw$^{-1}$ day$^{-1}$, or 9 $\mu$moles gfw$^{-1}$ hour$^{-1}$. The rate of nitrate depletion can be described with the same equation as given above for urea. Observed rate constants were $k_1$ 0.018 mmole gfw$^{-1}$ hour$^{-1}$ with ½ saturation at 0.5 mM. Nitrate uptake in greenhouse experiments was faster than uptake in laboratory experiments, but the difference was not statistically significant [data not shown]. Nitrate uptake was faster than urea uptake, but the difference was not statistically significant [data not shown].

No toxicity at a concentration of 2 mM nitrate was observed.

The information developed can be used to design fertilization regimes appropriate to a variety of circumstances. For example, consider the case of high productivity growth with culture density of 5 gfw liter$^{-1}$ or more, in which total dry weight accumulation is 30 gdw m$^{-2}$ day$^{-1}$ and in which a protein content of at least 25% is desired. (Low protein content gives less expensive growth requirements. High protein gives a greater value to the crop if it is used as animal feed.) To maintain a phosphate content of 0.4% requires uptake of 0.12 g m$^{-2}$ day$^{-1}$ of phosphorus, or 3.87 mmole m$^{-2}$ day$^{-1}$. If we choose conditions that give at least 90% uptake, we must provide at most 4.3 mmol m$^{-2}$ day$^{-1}$. For a 5 cm deep culture, this requires an initial concentration of 86.1 $\mu$M for daily water exchange, or 172 $\mu$moles for exchange every 48 hours. The time to 90% uptake may be calculated from the rate constant and the culture density using the equation:

$$t_{90} = \frac{2.3}{k_1 D}$$

where $t_{90}$ is the time in daylight hours required for 90% uptake, $k_1$ is the rate constant described earlier for phosphate uptake in liter gfw$^{-1}$ hour$^{-1}$, D is the culture density in gfw liter$^{-1}$, and 2.3 is the natural logarithm of 1/(1−0.9). For a culture density of 5 gfw liter$^{-1}$, 9.2 daylight hours are required for 90% uptake. Because there may be adverse effects of phosphate at concentrations significantly above 100 mM, daily exchange is preferred.

Nitrogen requirements for 25% protein will be satisfied by uptake of 1.2 g m$^{-2}$ day$^{-1}$ of nitrogen, or 86 mmol m$^{-2}$ day$^{-1}$. If we choose conditions that give at least 90% uptake, we must provide 95 mmol m$^{-2}$ day$^{-1}$. For a 5 cm deep culture, this requires an initial concentration of 1.9 mM nitrogen in some form. Since ammonium is toxic at this concentration, either nitrate or urea should be used. The amount of time required for 90% uptake can be calculated with the equation:

$$t_{90} = \frac{k_2 \ln(0.1) - (1 - 0.1)C_i}{K_1 D}$$

where $t_{90}$ is the time in hours required for 90% uptake, $k_1$ and $k_2$ are the rate constants described earlier for urea uptake, $C_i$ is the initial concentration of N in mM, and D is the culture density in gfw liter$^{-1}$. For a culture density of 5 gfw liters$^{-1}$, and initial concentration of 1.9 mM N, $t_{90}$ is 23.4 hours. A longer irrigation period is also acceptable, since the $t_{90}$ for 3.8 mM N is 46.2 hours, and urea is not toxic at this concentration.

In some cases it is desirable to grow cultures at lower density. For example, consider the case in which a culture with a density of 0.5 gfw liter$^{-1}$ is grown at a rate of increase of 40% per day, with a phosphate content of 0.4% and a protein content of 20%. Obviously an uptake period of several days will be required. Seven days (1 week) is a convenient period. In this time, culture density will increase from 0.5 to 5.3 gfw liter$^{-1}$. The dilute culture slows uptake at first, but within 2 days density is 1 gfw liter$^{-1}$, and $t_{90}$ for phosphate is 46 daylight hours, with 5 days of culture remaining. In seven days, a fresh weight accumulation of 4.8 gfw liter$^{-1}$, and a dry weight accumulation of 0.48 gdw liter$^{-1}$ is expected. This requires uptake of 1.9 mg phosphorus, so 60 mmol of phosphate. Assuming 90% uptake, 66.4 mM phosphate, which is in the non-toxic range must be provided. Similarly, the uptake of 15 mg of nitrogen is required, so 1071 mmol. Assuming 90% uptake, 1190 mM N, e.g., 595 mM urea must be provided. A check of $t_{90}$ for urea indicates a 90% uptake period of 76 hours for a 1 gfw liter$^{-1}$ culture, well within the five days remaining when this culture density is reached.

EXAMPLE 3: HIGH-YIELD GROWTH OF ENTEROMORPHA OUTDOORS IN PENNSYLVANIA

*Enteromorpha clathrata* cv. Berkeley was introduced into a one-square meter pond situated outdoors in Pennsylvania beginning May 13, 1996. During the experimental period, temperature varied from 30° F. (mild frost) to 93° F. Cultures were covered in the event of rain. Fertilizer was applied with water exchange on Mondays and Fridays. Fertilizer gave medium concentrations of 3 mM nitrogen as urea, 0.1 mM phosphate. On Wednesdays, water was exchanged but without fertilizer addition. The culture was allowed to grow for one week to fill the pond. After two weeks more, half of the culture was removed, rinsed in fresh water, air dried and weighed. The dry weight was 170 grams. A sample was oven dried in the laboratory, and water content was determined to be 8%. Thus the two week yield was 156 grams dry weight. The same fertilizer regime was continued for a further two weeks, and half of the culture was removed, washed in fresh water, air dried and weighed. The weight was 191 grams. A sample tested in the laboratory showed the water content to be 8%. Thus the two week yield was 176 grams dry weight. These yields correspond to per hectare yields of 1.56 and 1.76 tons respectively, or monthly yields of approximately 3.45 and 3.75 tons. They are close to the expected yield at this rate of fertilization of 160 grams dry weight per two weeks, with protein content of approximately 30%.

This experiment demonstrates the ability of Enteromorpha to grow at high yield in outdoor conditions through a wide temperature range. Planting of Enteromorpha in this case was started before corn planting in nearby fields, and first harvested when corn had just germinated.

EXAMPLE 4: RAPID GROWTH OF ENTEROMORPHA IN MEXICO

Approximately 4 kg fresh weight of Enteromorpha was introduced into a 5 cm deep, 400 square meter pond situated south of Ensenada, Mexico on Apr. 19, 1996. Fertilizer was applied on Mondays and Fridays with water exchange. Water was exchanged on Wednesdays without water exchange. Within 9 weeks, the pond was filled with a mat with a minimum thickness of 1 cm, occupying a volume of 4000 liters. Laboratory measurements indicated that 3 liters corresponds to 1 kg fresh weight, so estimated fresh weight in the poind was 1333 kg, indicating an average growth rate in the nine-week period of about 40 fold per week.

Wave action in the ponds was slight, and algae remained floating and well-distributed in the pond. There were no macroscopic indications of other algal species in the pond, nor any evidence of pests.

This experiment indicates that large-scale culture of Enteromorpha can be done successfully, with growth rates more than sufficient for commercial culture.

EXAMPLE 5: COMPOSITION OF PENNSYLVANIA-GROWN ENTEROMORPHA

Figure 6:
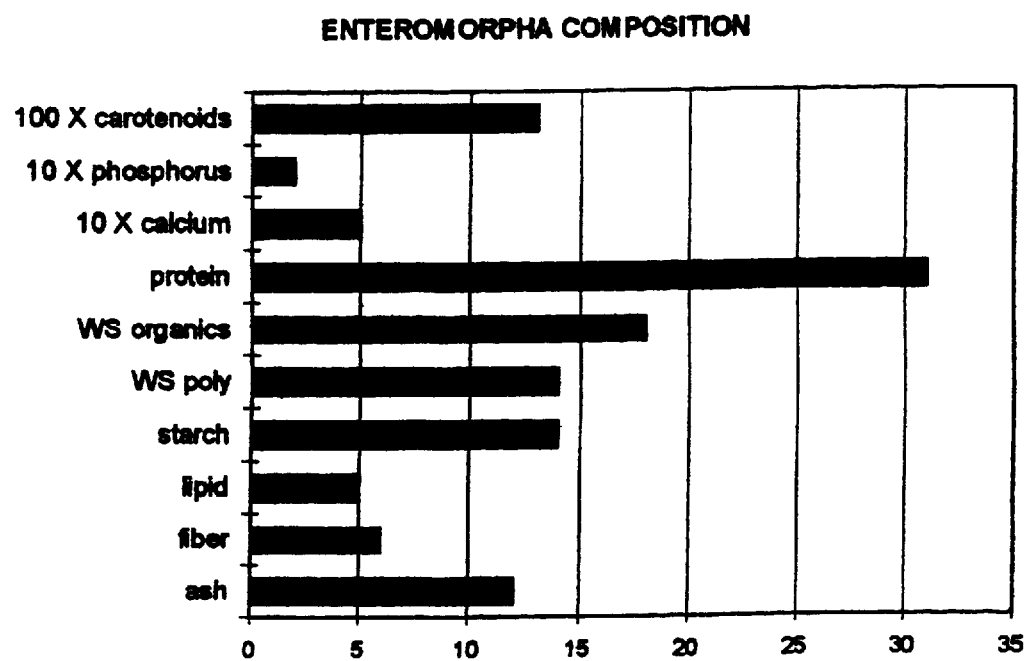
FIG. 6 is a bar graph showing the composition of Pennsylvania grown Enteromorpha.

Enteromorpha was grown in the greenhouse in Pennsylvania, washed in distilled water, air dried and milled in a hammer mill. Water content was determined by measuring change in weight after oven drying at 60° C. overnight. Other elements of composition are expressed on a dry weight basis. Protein was determined using a BCA protein assay kit (Pierce). Other experiments showed that results from this kit were comparable to estimation of protein by multiplication of total N by 6.25. Phosphate and calcium were determined by the Penn State Agricultural Testing Service. Starch was determined after removal of water-soluble polysaccharide overnight in distilled water at 70° C. Starch was measured as reducing sugar solubilized by perchlorate at room temperature, using phenol-sulfuric assay. Fiber occurred in two classes, water-soluble polysaccharide and perchlorate-insoluble polysaccharide, the latter designated in the figure as "fiber." Both were measured as reducing sugar equivalents using the phenol-sulfuric assay. Ash was determined from change in weight after heating overnight in a furnace at 900° C. The water soluble organic component was determined by gravimetric determination of the water soluble fraction of milled material, after removal of polysaccharide by ethanol precipitation, corrected for the measured ash and protein content of this fraction. FIG. 6 summarizes the composition results as percentage of dry weight.

EXAMPLE 6: COMPARISON OF ENTEROMORPHA FEED OF EXAMPLE 5 WITH ALFALFA LEAF MEAL COMPOSITION OF *ENTEROMORPHA CLATHRATA*

Figure 7:
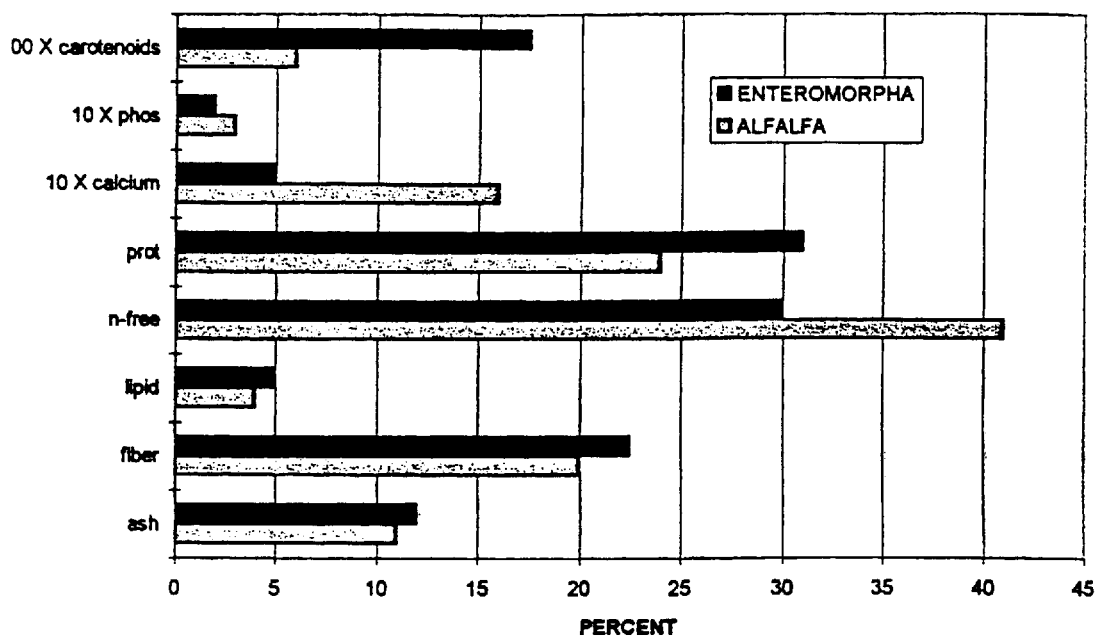
FIG. 7 is a bar graph showing the comparison of Enteromorpha and alfalfa meal.

The significance of the composition of the Enteromorpha of Example 5 to the use of Enteromorpha as animal feed is demonstrated in FIG. 7 below which compares the composition of Enteromorpha and high protein alfalfa leaf meal. In this figure, the two classes of fiber are pooled into a single category. Further, starch and water-soluble organics are pooled into a single category "n-free" referring to the nitrogen free extract, a common measure of the readily digested but not protein fraction of feed-stuffs. Note the similarity between Enteromorpha and high protein alfalfa leaf meal.

EXAMPLE 7: USE OF *ENTEROMORPHA CLATHRATA* AS A FEED FOR CHICKENS

INTRODUCTION

The purpose of this example is to show the utility of *Enteromorpha clathrata* seaweed meal as an ingredient in chicken feed as a source of xanthophylls. In some cases, it is desirable to supplement diets with ingredients high in xanthophylls (carotenoids with one or more hydroxl groups). The color of egg yolks depends on dietary xanthophylls, as does the color of the skin of the chicken. These color facts can be important elements of consumer appeal in eggs and in broiler chickens. This study was intended to determine whether the xanthophylls of Enteromorpha added to feed were effective in coloring egg yolks. Additionally, the study was intended to detect any toxic effect sufficient to cause diminished productivity, or any adverse effect on feed consumption.

Other feed ingredients that contain significant amounts of xanthophylls include alfalfa, yellow corn, corn gluten meal, algae meal (e.g., Spirulina), and marigold petal meal or extract. Artificial pigmenting agents are also available. The most commonly used xanthophyll sources in the United States are yellow corn and corn gluten meal. Alfalfa is often included in chicken diets, but at a level too low to make a significant contribution to xanthophyll content. Algae meal and marigold petal meal have high xanthophyll levels, but they are more expensive sources and only used if especially high xanthophyll levels are desired. The principal xanthophyll of Enteromorpha is lutein. This is also the most common xanthophyll found in the leaves of terrestrial plants, and it is known to be used efficiently as a chicken egg yolk and skin coloring compound.

The green alga Ulva, which is closely related to Enteromorpha, has previously been fed to chickens without adverse effect on rate of weight gain.

MATERIALS AND METHODS

SEAWEED MEAL. *Enteromorpha clathrata* was grown in a greenhouse in Pennsylvania. The seaweed was air dried using forced air at 40° C. to a water content of 9%. Dried seaweed was milled with a hammermill to a fine powder, particle size less than 50 microns. The meal was stored in the dark at −20° C. until it was incorporated into the feed mix.

MEASUREMENT OF CAROTENOIDS. To confirm identity of carotenoids, lipids were extracted with methanol; acetone 1:1 at room temperature, dried under vacuum, redissolved in 95% ethanol and saponified using 1/10 volume aqueous sodium hydroxide and boiling for 3 minutes. Carotenoids were partitioned into petroleum ether. Xanthophylls were then partitioned in 95% methanol, leaving carotene in the ether phase. Chromatography on alumina of the xanthophyll fraction gave a major peak with absorption characteristic of lutein, a much smaller minor peak possibly due to violaxanthin. 80% of the absorbance at 450 mn of the total carotenoid extract was due to xanthophyll.

For routine measurements, the rapid extraction method of Livingston was used, and the resultant total carotenoid measure was multiplied by 0.8 to estimate xanthophyll content. Addition of a known quantity of xanthophyll to this assay showed that extraction from feed is less efficient than from more concentrated sources such as Enteromorpha, so estimates of feed xanthophyll were multiplied by a factor of 1.33, the figure deduced from xanthophyll addition experiments. There were no significant differences between xanthophyll measurements made at the time of feed mixing and four weeks later.

FEEDING CHICKENS. (2 cages of four for each treatment) were allowed free access to feed. Base feed was yellow corn with supplements, including corn gluten meal for the high xanthophyll control. Base feed was barley and wheat with supplements including corn gluten meal for the low xanthophyll control. Supplemented rations were the low control with 1.5% Enteromorpha meal added, and no other changes.

Los and high control diets were essentially isocaloric and isonitrogenous. Total amount of feed consumed in the 3½ weeks of the experiment was determined for each feeding regime.

EGG SCORING. Eggs were collected daily from each cage, and numbers recorded by cage. A sample of eggs were broken and yolk color scored at weekly intervals. A sample of eggs were weighed to determine average egg weight. T-tests were used to determine whether differences between treatments were statistically significant.

RESULTS AND DISCUSSION

XANTHOPHYLL CONTENT OF SEAWEED MEAL AND MIXED FEEDS.

Table 4 below shows the measured xanthophyll content of seaweed meal and the three feed mixes used, expressed on a dry weight basis. Data are averages of three samples per treatment. All three treatments are significantly different ($p<0.01$).

TABLE 4

| XANTHOPHYLL CONTENT (PPM) | | | |
|---|---|---|---|
| Seaweed meal | High control | Low control | Supplemented |
| 962 | 24 | 14 | 28 |

EGG YOLK COLOR. Table 5 below shows the averaged yolk color scores taken at weekly intervals. "Week 0" scores reflect the previous history of feeding on the high control diet. At least 10 eggs were scored each week for each treatment. The low control is significantly different from both the high control and the supplemented treatments after week 0 ($p<0.01$). The high control and supplemented treatments are not significantly different ($p>0.05$).

TABLE 5

| YOLK COLOR | | | |
|---|---|---|---|
| Week: | High Control | Low Control | Supplemented |
| 0 | 5.9 | 6 | 6.1 |
| 1 | 6.3 | 4.9 | 6.5 |
| 2 | 6.5 | 4.1 | 7.0 |
| 3 | 6.3 | 3.9 | 6.6 |

EGG NUMBER AND SIZE. Table 6 shows the number of eggs produced in each week of the experiment. The weekly egg production is not significantly different between treatments ($p>0.05$).

TABLE 6

| EGG NUMBER | | | |
|---|---|---|---|
| Week: | High Control | Low Control | Supplemented |
| 1 | 43 | 47 | 48 |
| 2 | 50 | 51 | 49 |
| 3 | 51 | 54 | 54 |
| TOTAL | 144 | 152 | 151 |
| Eggs/hen-day | 0.86 | 0.9 | 0.9 |

FEED CONSUMPTION. Table 7 shows the amount of feed consumed for the different treatments over the course of the experiment, expressed both as a total amount and as feed per hen per day. There are no significant differences in feed consumption between treatments ($p>0.05$).

TABLE 7

FEED CONSUMPTION

| Treatment | Feed Consumed | Feed Per Hen Per Day (g) |
| --- | --- | --- |
| High Control | 19 | 95 |
| Low Control | 19.15 | 95.75 |
| Supplemented | 19.51 | 97.55 |

CONCLUSIONS

At a supplementation rate of 1.5%, Enteromorpha meal is without adverse effects on feed consumption or laying hen performance. The xanthophyll content of Enteromorpha is used with the same efficiency as corn xanthophyll in coloring egg yolks.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

I claim:

1. A method for the high-yield, agricultural production of isolated *Enteromorpha clathrata*, comprising the steps of:

(a) providing a pond for holding a volume of liquid:

(b) supplying a first volume of water to the pond to a depth of between 1 cm and 20 cm, the water comprising at least one of brackish and seawater and having a salinity not exceeding 70 ppt, supplemented with a fertilizer having a nitrogen to phosphate molar ratio of approximately between 10 and 40 to 1, wherein said water is conducive to growing isolated *Enteromorpha clathrata*;

(c) introducing isolated *Enteromorpha clathrata* into said conducive water;

(d) growing said isolated *Enteromorpha clathrata* for a predetermined time, wherein said conducive water becomes less conducive to growing said isolated *Enteromorpha clathrata* after said time;

(e) withdrawing at least partially said less conducive water after said predetermined time;

(f) refilling said pond to a depth of between 1 cm to 20 cm with a second volume of water, the second volume of water comprising at least one of brackish and seawater and having a salinity not exceeding 70 ppt, supplemented with a fertilizer having a nitrogen to phosphate molar ratio of approximately between 10 and 40 to 1, wherein said water is conducive to growing isolated *Enteromorpha clathrata* ;

(g) repeating steps d, e, and f wherein said isolated *Enteromorpha clathrata* grows into a layer of filaments, extending above the surface of the water and being exposed to the air;

wherein said isolated *Enteromorpha clathrata* grows at a rate of approximately 5 to 40 grams dry weight per square meter per day.

2. A method according to claim 1 wherein the water is filled to a depth of 5 cm in steps (b) and (f), wherein the fertilizer of steps (b) and (f) is urea in a concentration of approximately 1 mM and phosphoric acid in a concentration of approximately 100 micromolar and the nitrogen to phosphate ratio molar ratio is approximately 20:1, and wherein the predetermined time of step (d) is approximately between 1 to 3 days.

3. A method according to claim 1 wherein the water is filled to a depth of 5 cm in steps (b) and (f), wherein the fertilizer of steps (b) and (f) is urea in a concentration of approximately 1.5 mM and phosphoric acid in a concentration of approximately 0.1 mM, and the nitrogen to phosphate ratio molar ratio is approximately 30:1, and wherein the predetermined time of step (d) is approximately between 1 to 2 days.

4. A method according to claim 1 wherein the water is filled to a depth of 5 cm in steps (b) and (f), wherein the fertilizer of steps (b) and (f) is phosphoric acid in a concentration of 100 micromolar which is added with each repetition of step (f) and urea in a concentration of 2 mM which is added with every other repetition of step (f), and wherein the predetermined time of step (d) is approximately one day.

5. A method according to claim 1 wherein the first and second volumes of water are 50 liters per square meter of pond surface area.

6. A method according to claim 1 wherein the step of refilling the pond of step (f) takes less than two (2) hours.

7. A method according to claim 1 wherein the source of the nitrogen is urea and the source of the phosphate is phosphoric acid.

8. A method according to claim 1 wherein the fertilizer is further comprised of at least one of $FeCl_3$, $MnSO_4$, $ZnCl_2$, $CuCl_2$, $CoSO_4$, and ammonium molybdate.

9. A method according to claim 1 wherein the isolated *Enteromorpha clathrata* is washed with water after the less conducive water has been withdrawn from the pond in step (e) and before the pond has been refilled with the more conducive water in step (f) in order to reduce the populations of unicellular algae in the pond.

10. A method according to claim 1 wherein the depth to which said pond is filled in step (b) or refilled in step (f) is between 3 cm and 7 cm.

11. A method according to claim 1 wherein said isolated *Enteromorpha clathrata* is isolated *Enteromorpha clathrata* cv. "Berkeley".

12. A method according to claim 1 wherein said isolated *Enteromorpha clathrata* is a haploid derivative of isolated *Enteromorpha clathrata* cv. "Berkeley".

13. A method according to claim 12 wherein said haploid derivative is selected from the group consisting of ZS1, ZS2, ZS3, ZS4, ZS5, ZS6, ZS7, ZS8, ZS9, ZS10, ZS11, ZS12, ZS13, ZS14, and ZS15.

14. A method according to claim 1 wherein said conducive water has a salinity not exceeding 300 ppt.

15. A method according to claim 1 wherein said predetermined time of step (d) is approximately one day.

16. A method according to claim 1 wherein the temperature of the water in the pond is between 20° C. and 40° C.

17. Isolated *Enteromorpha clathrata* grown according to claim 1.

18. Isolated *Enteromorpha clathrata* grown according to claim 1, wherein the isolated *Enteromorpha clathrata* is composed of approximately 30% protein.

19. A method according to claim 1 wherein the first and second volumes of water have a pH of between 7.5 and 9.5.

20. A method according to claim 1 wherein the second volume of water is only supplemented with the fertilizer in every other repetition of step (f).

21. A method according to claim 1 wherein the fresh weight of the isolated *Enteromorpha clathrata* increases by approximately 40% per day.

22. A method according to claim 1 wherein the isolated *Enteromorpha clathrata* utilizes approximately 90% of the fertilizer during the growth step of step (d).

23. A method for the high-yield, agricultural production of isolated *Enteromorpha clathrata*, comprising the steps of:

(a) providing a pond for holding a volume of liquid;

(b) supplying a first volume of water to the pond to a depth of between 1 cm and 20 cm, the water comprising at least one of brackish and seawater and having a salinity not exceeding 70 ppt, supplemented with a fertilizer, wherein said water is conducive to growing isolated *Enteromorpha clathrata* ;

(c) introducing isolated *Enteromorpha clathrata* into said conducive water;

(d) growing said isolated *Enteromorpha clathrata* for a predetermined time, wherein said conducive water becomes less conducive to growing said isolated *Enteromorpha clathrata* after said time;

(e) withdrawing at least partially said less conducive water after said predetermined time;

(f) refilling said pond to a depth of between 1 cm to 20 cm with a second volume of water, the second volume of water comprising at least one of brackish and seawater and having a salinity not exceeding 70 ppt, supplemented with a fertilizer, wherein said water is conducive to growing isolated *Enteromorpha clathrata*; and (g) repeating steps d, e, and f wherein said isolated *Enteromorpha clathrata* grows into a layer of filaments, extending above the surface of the water and being exposed to the air.

24. A method according to claim 23 wherein the water is filled to a depth of approximately 5 cm in steps (b) and (f), wherein the fertilizer of steps (b) and (f) is urea in a concentration of approximately 1 mM and phosphoric acid in a concentration of approximately 100 micromolar and the nitrogen to phosphate ratio molar ratio is approximately 20:1, and wherein the predetermined time of step (d) is approximately between one to three days.

25. A method according to claim 23 wherein the water is filled to a depth of approximately 5 cm in steps (b) and (f), wherein the fertilizer of steps (b) and (f) is urea in a concentration of approximately 1.5 mM and phosphoric acid in a concentration of approximately 0.1 mM, and the nitrogen to phosphate ratio molar ratio is approximately 30:1, and wherein the predetermined time of step (d) is approximately between one to two days.

26. A method according to claim 23 wherein the water is filled to a depth of 5 cm in steps (b) and (f), wherein the fertilizer of steps (b) and (f) is phosphoric acid in a concentration of 100 micromolar which is added with each repetition of step (f) and urea in a concentration of 2 mM which is added with every other repetition of step (f), and wherein the predetermined time of step (d) is approximately one day.

27. A method according to claim 23 wherein the step of refilling the pond of step (f) takes less than two (2) hours.

28. A method according to claim 23 wherein the step of refilling the pond of step (e) takes less than two (2) hours.

29. A method according to claim 23 wherein the maximum depth to which said pond is filled or refilled is between 1 cm and 20 cm.

30. A method according to claim 23 wherein the maximum depth to which said pond is filled or refilled is between 3 cm and 7 cm.

31. A method according to claim 23 wherein said isolated *Enteromorpha clathrata* is isolated *Enteromorpha clathrata* cv. "Berkeley".

32. A method according to claim 1 wherein said isolated *Enteromorpha clathrata* is a haploid derivative of isolated *Enteromorpha clathrata* cv. "Berkeley".

33. A method according to claim 32 wherein said haploid derivative is selected from the group consisting of ZS1, ZS2, ZS3, ZS4, ZS5, ZS6, ZS8, ZS9, ZS10, ZS11, ZS12, ZS13, ZS14, and ZS15.

34. A method according to claim 23 wherein said conducive water has a salinity not exceeding 300 ppt.

35. A method according to claim 23 wherein said conducive water has a salinity not exceeding 70 ppt.

36. A method according to claim 23 wherein the average rate of of the isolated *Enteromorpha clathrata* in step (d) is between approximately 5 to 40 grams dry weight per square meter per day.

37. A method according to claim 23 wherein said predetermined time of step (c) is one day.

38. A method according to claim 23 wherein the temperature of the water in the pond is between 20° C. and 40° C.

39. A method according to claim 23 wherein the pond is refilled with more conducive water in step (f) to the same depth as in step (b).

40. A method according to claim 23 wherein the isolated *Enteromorpha clathrata* is washed with water after the less conducive water has been withdrawn from the pond in step (e) and before the pond has been refilled with the more conducive water in step (f) in order to reduce the populations of unicellular algae in the pond.

41. A method according to claim 23 wherein at least one antibiotic is added to the water to eliminate organisms other than isolated *Entermorpha clathrata* from the pond.

42. A method according to claim 23 wherein the water is treated with copper to eliminate organisms other than isolated *Entermorpha clathrata* from the pond.

43. A method according to claim 23 wherein said fertilizer is selected from the group consisting of ammonia, ammonium, nitrate, urea, phosphate, and phosphoric acid.

44. A method according to claim 23 wherein the fertilizer has a nitrogen to phosphate molar ratio of approximately 30 to 1.

45. A method according to claim 44 wherein the source of the nitrogen is urea and the source of the phosphate is phosphoric acid.

46. A method according to claim 45 wherein the fertilizer is further comprised of $FeCl_3$, $MnSO_4$, $ZnCl_2$, $CuCl_2$, $CoSO_4$, and ammonium molybdate.

47. Isolated *Enteromorpha clathrata* grown according to claim 1.

48. Isolated *Enteromorpha clathrata* grown according to claim 1, wherein the isolated *Enteromorpha clathrata* is composed of approximately 30% protein.

49. A method according to claim 23 wherein the first and second volumes of water have a pH of between 7.5 and 9.5.

50. A method according to claim 23 wherein the second volume of water is only supplemented with the fertilizer in every other repetition of step (f).

51. A method according to claim 23 wherein the fresh weight of the isolated *Enteromorpha clathrata* increases by approximately 40% per day.

52. A method according to claim 1 wherein the isolated *Enteromorpha clathrata* utilizes approximately 90% of the fertilizer during the growth step of step (d).

53. A method of producing feed for mammals and poultry comprising growing isolated *Enteromorpha clathrata* according to claim 1 and further comprising the steps of:

a) removing said less conducive water from said isolated *Enteromorpha clathrata* filaments to allow said isolated *Enteromorpha clathrata* filaments to partially dry;

b) drying said partially dry isolated *Enteromorpha clathrata* filaments to less than 15% water content by weight; and c) milling said dried isolated *Enteromorpha clathrata* filaments to powder for use in producing feed.

54. A nutritious feed for mammals and poultry produced according to claim 53.

55. The nutritious feed of claim 54, wherein the feed has a protein content of approximately 30%.

56. The nutritious feed of claim 54, wherein the feed contains xanthophyll.

57. A method of producing feed for mammals and poultry comprising growing isolated *Enteromorpha clathrata* according to claim 1 and further comprising the steps of:

a) removing said less conducive water from said isolated *Enteromorpha clathrata* filaments to allow said isolated *Enteromorpha clathrata* filaments to partially dry;

b) drying said partially dry isolated *Enteromorpha clathrata* filaments to less than 50% water content by weight; and c) pressing, rolling or extruding said dried isolated *Enteromorpha clathrata* filaments to form pellets or sheets; and d) drying of said pellets or sheets to a water content of less than 20%.

58. A nutritious feed for mammals and poultry produced according to claim 57.

59. The nutritious feed of claim 58, wherein the feed has a protein content of approximately 30%.

60. The nutritious feed of claim 58, wherein the feed contains xanthophyll.

61. A method for producing feed for mammals and poultry, comprising the steps of:

a) providing an pond for holding a volume of a liquid;

b) supplying a first volume of water to a depth of between 1 cm and 20 cm to the pond, the water comprising at least one of brackish and seawater and having a salinity not exceeding 300 ppt and being supplemented with a fertilizer having a nitrogen to phosphate molar ratio of approximately between 10 and 40 to 1, wherein said water is conducive to growing a isolated *Enteromorpha clathrata;* c) introducing said isolated *Enteromorpha clathrata* into said conducive water;

d) growing said isolated *Enteromorpha clathrata* for a time period of between twelve hours to three days, wherein said conducive water becomes less conducive to growing said isolated *Enteromorpha clathrata* after said time period;

e) withdrawing from said pond between 1% to 100% of the less conducive water after said time period;

f) refilling said pond to a depth of between 1 cm and 20 cm with a second volume of water having a salinity not exceeding 300 ppt, comprising at least one of brackish and seawater, supplemented with a fertilizer having a nitrogen to phosphate molar ratio of approximately between 10 and 40 to 1, wherein said water is conducive to growing said isolated *Enteromorpha clathrata;* g) repeating steps d, e, and f, wherein said isolated *Enteromorpha clathrata* grows into a layer of filaments, a portion of the filaments extending above the surface of the water and being exposed to the air, and wherein said isolated *Enteromorpha clathrata* grows at a rate of approximately 5 to 40 grams dry weight per square meter per day;

h) removing all of the less conducive water from said filaments of the *Enteromorpha clathrata;* i) drying the isolated *Enteromorpha clathrata* filaments; and j) processing the *Entermorpha clathrata* filaments into feed for mammals and poultry.

* * * * *